(12) United States Patent
Summers et al.

(10) Patent No.: US 7,037,660 B2
(45) Date of Patent: May 2, 2006

(54) METHODS FOR DETECTING AND QUANTIFYING BINDING AND INHIBITION OF BINDING OF SPECIES TO NUCLEIC ACIDS

(75) Inventors: Jack Summers, Baltimore, MD (US); Michael Sturgess, Quakertown, PA (US); John Shimko, Baltimore, MD (US)

(73) Assignee: Message Pharmaceuticals, Malvern, PA (US)

( * ) Notice: Subject to any disclaimer, the term of this patent is extended or adjusted under 35 U.S.C. 154(b) by 590 days.

(21) Appl. No.: 10/289,057

(22) Filed: Nov. 6, 2002

(65) Prior Publication Data
US 2003/0148343 A1 Aug. 7, 2003

Related U.S. Application Data

(60) Provisional application No. 60/332,969, filed on Nov. 6, 2001.

(51) Int. Cl.
 *C12Q 1/68* (2006.01)
 *C07H 21/02* (2006.01)
 *C07H 21/04* (2006.01)

(52) U.S. Cl. .......................... 435/6; 536/23.1; 536/24.3
(58) Field of Classification Search .................... 435/6; 536/23.1, 24.3
See application file for complete search history.

(56) References Cited

U.S. PATENT DOCUMENTS

| | | | |
|---|---|---|---|
| 4,880,008 A | 11/1989 | Lauffer | |
| 5,401,491 A | 3/1995 | Sadler et al. | |
| 5,460,799 A | 10/1995 | Elgavish et al. | |
| 5,804,390 A | 9/1998 | Fesik et al. | |
| 6,043,024 A | 3/2000 | Fesik et al. | |

OTHER PUBLICATIONS

Allain, et al. Divalent Metal Ion Binding to a Conserved Wobble Pair Defining the Upstream Site of Cleavage of Group I Self-Splicing Introns, Nucleic Acids Research, 1995, 23:341-350.

Arnold, et al. Poliovirus RNA-dependent RNA Polymerase (3D$^{pol}$), The Journal of Biological Chemistry, 1999, 274:37060-37069.

Batey, et al. Tertiary Motifs in RNA Structure and Folding, Angewandte Chemie International Ed., 1999, 38:2327-2343.

Bracco, et al. NMR Detection of Superoxide Dismutases in the Rat Brain, PET and NMR: New Perspectives in Neuroimaging and in Clinical Chemistry, 1986, 315-324.

Butcher, et al. Determination of Metal Ion Binding Sites Within the Hairpin Ribozyme Domains by NMR, Biochemistry, 2000, 39:2174-2182.

Danchin, et al. Proton Magnetic Relaxation Study of the Manganese-Transfer-RNA Complex, The Journal of Chemical Physics, 1970, 53:3599-3609.

Farrow, et al. Backbone Dynamics of a Free and a Phosphopeptide-Complexed Src Homology 2 Domain Studied by $^{15}$N NMR Relaxation, Biochemistry, 1994, 33:5984-6003.

Gebhardt, et al. RNA Aptamers to S-Adenosylhomocysteine: Kinetic Properties, Divalent Cation Dependency, and Comparison with Anti-S-Adenosylhomocysteine Antibody, Biochemistry, 2000, 39:7255-7265.

Hermann, et al. Aminoglycoside Binding to the Hammerhead Ribozyme: A General Model for the Interaction of Cationic Antibiotics with RNA, Journal of Molecular Biology, 1998, 276:903-912.

Hingerty, et al. Stabilization of the Tertiary Structure of Yeast Phenylalanine tRNA by $[Co(NH_3)_6]^{3+}$, X-Ray Evidence for Hydrogen Bonding to Pairs of Guanine Bases in the Major Groove, Biochimica et Biophysica Acta, 1982, 697:78-82.

Hoch, et al. Antibiotic Inhibition of RNA Catalysis: Neomycin B Binds to the Catalytic Core of the td Group I Intron Displacing Essential Metal Ions, Journal of Molecular Biology, 1998, 282:557-569.

Hoogstraten, et al. Structural Analysis of Metal Ion Ligation to Nucleotides and Nucleic Acids Using Pulses EPR Spectroscopy, Journal of the American Chemical Society, 2002, 124:834-842.

Horton, et al. Electron Paramagnetic Resonance Spectroscopic Measurement of $Mn^{2+}$ Binding Affinities to the Hammerhead Ribozyme and Correlation with Cleavage Activity, Biochemistry, 1998, 37:18094-18101.

Kandegedara, et al. Noncomplexing Tertiary Amines as "Better" Buffers Covering the Range of pH 3-11. Temperature Dependence of Their Acid Dissoclation Constants, Analytical Chemistry, 1999, 71:3140-3144.

(Continued)

*Primary Examiner*—Ethan Whisenant
(74) *Attorney, Agent, or Firm*—Clark & Elbing LLP; Kristina Bieker-Brady

(57) ABSTRACT

The invention features methods for detecting and quantifying the binding or inhibition of binding of species to biopolymers, e.g., nucleic acids. The invention is based on the use of probes that have magnetic relaxation properties that are affected by the presence of paramagnetic metal ions, e.g., $Mn^{2+}$. Any class of biopolymer that binds metal ions at its active site or uses metal ion cofactors can be studied using these methods.

41 Claims, 15 Drawing Sheets

OTHER PUBLICATIONS

Laing, et al. Stabilization of RNA Structure by Mg Ions, Specific and Non-specific Effects, Journal of Molecular Biology, 1994, 237:577-587.

Laundon, et al. Cationic Metals Promote Sequence-Directed DNA Bending, Biochemistry, 1987, 26:3759-3762.

Maderia, et al. Metal Interactions with a GAAA RNA Tetraloop Characterized by $^{31}$P NMR and Phosphorothioate Substitutions, Biochemistry, 2000, 39:8193-8200.

Mikkelsen, et al. Inhibition of RNase P RNA Cleavage by Aminoglycosides, Proceedings of the National Academy of Sciences, USA, 1999, 96:6155-6160.

Mikkelsen, et al. Aminoglycoside Binding Displaces a Divalent Metal Ion in a tRNA-Neomycin B Complex, Nature Structural Biology, 2001, 8:510-514.

Morrissey, et al. $Mn^{2+}$—Nitrogen Interactions in RNA Probed by Electron Spin-Echo Envelope Modulation Spectroscopy: Application to the Hammerhead Ribozyme, Journal of the American Chemical Society, 1999, 121:9215-9218.

Orr, et al. Protein and $Mg^{2+}$-Induced Conformational Changes in the S15 Binding Site of 16 S Ribosomal RNA, Journal of Molecular Biology 1998, 275:453-464.

Ott, et al. Proton NMR Studies of Manganese Ion Binding to tRNA-Derived Acceptor Arm Duplexes, Nucleic Acids Research, 1993, 21:5859-5864.

Peacocke, et al. Proton Magnetic Relaxation in Solutions of *E. coli* Ribosomal RNA Containing $Mn^{2+}$ Ions, Molecular Physics, 1969, 16:177-189.

Rigo, et al. Nuclear Magnetic Relaxation of $^{19}$F as a Novel Assay Method of Superoxide Dismutase, The Journal of Biological Chemistry, 1979, 254:1759-1760.

Rigo, et al. $^{19}$F-Nuclear Magnetic Relaxation by Superoxide Dismutase as an Enzymic Method for the Detection of Superoxide Ion, FEBS Letters, 1981, 132:78-80.

Schimmel, et al. Transfer RNA in Solution: Selected Topics, Annual Reviews in Biophysics and Bioengineering, 1980, 9:181-221.

Shui, et al. Structure of the Potassium Form of CGCGAAT-TCGCG: DNA Deformation by Electrostatic Collapse Around Inorganic Cations, Biochemistry, 1998, 37:16877-16887.

Shui, et al. The B-DNA Dodecamer at High Resolution Reveals a Spine of Water on Sodium, Biochemistry, 1998, 37:8341-8355.

Summers, et al. $^{31}$P NMR Probes of Chemical Dynamics: Paramagnetic Relaxation Enhancement of the $^1$H and $^{31}$P NMR Resonances of Methyl Phosphite and Methylethyl Phosphate Anions by Selected Metal Complexes, Inorganic Chemistry, 2001, 40:6547-6554.

Viglino, et al. The Binding of Fluoride Ion to Bovine Cuprozinc Superoxide Dismutase as Studied by $^{19}$F Magnetic Relaxation, Journal of Magnetic Resonance, 1979, 34:265-274.

Wilson, et al. Folding of A+U-Rich RNA Elements Modulates AUF1 Binding, The Journal of Biological Chemistry, 2001, 276:8695-8704.

Yu, et al. Avoiding Interferences from Good's Buffers: A Contiguous Series of Noncomplexing Tertiary Amine Buffers Covering the Entire Range of pH 3-11, Analytical Biochemistry, 1997, 253:50-56.

Zimmermann, et al. Molecular Interactions and Metal Binding in the Theophylline-Binding Core of an RNA Aptamer, RNA, 2000, 6:669-667.

MeOPH            EtPH

A. RNA secondary structures

RRE1　　　RRE2　　　A-site

B. neomycin b

C. RSG1.2

5'-RDRRRRGSRPSGAERRRRRAAAA-3'

METHODS FOR DETECTING AND
QUANTIFYING BINDING AND INHIBITION
OF BINDING OF SPECIES TO NUCLEIC
ACIDS

CROSS-REFERENCE TO RELATED
APPLICATIONS

This application claims benefit of priority from U.S. Provisional Application No. 60/332,969, filed Nov. 6, 2001, hereby incorporated by reference.

BACKGROUND OF THE INVENTION

The invention relates to the fields of drug discovery and nuclear magnetic resonance spectroscopy.

Nucleic acids (DNA and RNA) are biopolymers in which each monomer contains a negatively charged phosphate ester group. This large negative charge is balanced by interaction of the nucleic acid with small cationic species, including protonated amines, and monovalent and divalent metal ions. In addition to non-specific electrostatic interactions, structured nucleic acids have specific metal ion binding sites. Examples of specific divalent metal ion binding by RNA molecules can be seen in the group III-V intron of the tetrahymina ribozyme, ribosomal RNA, and RNA aptamers. Such interactions may be mediated by direct coordination of the bases or phosphates to the metal ion, or by hydrogen bonding between water molecules coordinated to the metal ion and the nucleotide bases.

Divalent metal ions can be bound by either specific interactions with discrete metal binding sites or non-specifically via coulombic interaction. For non-specific interactions, binding is described by the polyelectrolyte condensation model. Binding affinities are dependant on the ionic strength of the solution and the nature of the cationic form of the supporting electrolyte. This dependence on the nature and concentration of the supporting electrolyte is to be expected since the divalent ion will have to compete with the electrolyte cation for both specific and non-specific interactions. Non-specific affinities can be represented by interactions of $Mg^{2+}$ with poly-uridine (poly-U). In 10 mM NaCl, 96 µM $Mg^{2+}$, the apparent association constant for poly-U/Mg binding is reported as $1.86 \times 10^3$ $M^{-1}nt^{-1}$, where nt is the number of nucleotides in the strand. When other bases are incorporated into the RNA strand, binding of the metal to the bases is possible. Under similar conditions to those of the poly-U study, poly-A has a reported $Mg^{2+}$ binding affinity of $10.7 \times 10^3$ $M^{-1}nt^{-1}$, a 5.7 fold increase over poly-U. This difference must be attributed to contributions from base/metal interactions, since the two nucleic acids share the same charge distribution along their backbones. Specific metal binding sites having affinities in the micromolar range have been reported for transfer RNAs and the hammerhead ribozyme. Up to 8 $Mn^{2+}$ ions bind to the Hammerhead ribozyme with $K_D$ values ranging from 4 to 500 µM.

Since divalent metal ions are necessary structural elements of some molecules of RNA and since the RNA molecules exchange bound ions with ions free in the bulk solution, sites for binding metal ions are natural candidates for drug targets. Aminoglycoside antibiotics are believed to act by displacing divalent metal ions from specific binding sites on RNA. Aminoglycosides are reported to displace $Mg^{2+}$ from specific sites on a variety of RNA molecules including a model of the ribosomal A, the hammerhead ribozyme, the tetrahymina group I intron, and RNase P.

The magnetic relaxation properties of NMR active nuclei can be very sensitive to paramagnetic metal ions. Thermodynamic and structural aspects of macromolecules that bind metal ions have been studied by exploiting this effect. In the majority of works, the effects of the paramagnetic metal ion on the magnetic resonances of $^1H$ of the biological molecule have been determined in order to study the geometry of the metal binding site. In addition, there have been a more limited number of studies where the metal binding sites have been examined using external small species such as water or fluoride ion.

Paramagnetic relaxation enhancement of the magnetic resonance of $^1H$ nuclei of solvent water has been used to study metal binding by a variety of biological macromolecules qualitatively. This approach has been used to characterize the binding of $Mn^{2+}$ to transfer RNA and ribosomal RNA among other molecules. Another approach for paramagnetic relaxation enhancement that has seen limited use is the use of $^{19}F$ fluoride as a probe. Relaxation enhancements of this resonance by superoxide dismutases have been reported. Metal ion binding studies where the perturbations observed are of the macromolecular $^1H$ resonances have also been reported. Molecules studied include ribozymes and smaller RNA fragments. Water $^1H$ resonances, however are not very sensitive to paramagnetic relaxation, and $^{19}F$ measurements require $^{19}F$ NMR.

There exists a need for sensitive methods for measuring the binding and inhibition of binding of species to nucleic acids. These methods may find use in the field of drug discovery.

SUMMARY OF THE INVENTION

The invention provides methods for detecting and quantifying the binding or inhibition of binding of species, e.g., candidate therapeutic agents, to biopolymers, e.g., nucleic acids. The invention is based on the use of probes that have magnetic relaxation properties that are affected by the presence of paramagnetic metal ions. Although the following description focuses on nucleic acids, any class of biopolymer that binds metal ions at its active site or uses metal ion cofactors can be studied using these methods.

In one aspect, the invention features a method of detecting the binding of a species to a nucleic acid that includes the steps of measuring a magnetic relaxation property of a probe in a first solution using nuclear magnetic resonance spectroscopy, wherein the first solution includes the nucleic acid, a first concentration of the species, a paramagnetic metal ion, and the probe; measuring the magnetic relaxation property of the probe in a second solution using nuclear magnetic resonance spectroscopy, wherein the second solution includes the nucleic acid, a second concentration of the species, a paramagnetic metal ion, and the probe; and comparing the relaxation properties measured, wherein a difference in the relaxation properties indicates the binding of the species to the nucleic acid. In one embodiment, the magnetic relaxation properties of the probe are correlated with the first and second concentrations of the species, thereby quantifying the binding of the species to the nucleic acid.

The invention further features a method of detecting the binding of a paramagnetic metal ion to a nucleic acid including the steps of measuring a magnetic relaxation property of a probe in a first solution using nuclear magnetic resonance spectroscopy, wherein the first solution includes a first concentration of the paramagnetic metal ion, the nucleic acid, and the probe; measuring the magnetic relaxation property of the probe in a second solution using nuclear magnetic resonance spectroscopy, wherein the second solution includes a second concentration of the paramagnetic metal ion, the nucleic acid, and the probe; and comparing the relaxation properties measured, wherein a difference in the relaxation properties indicates the binding of the paramagnetic metal ion to the nucleic acid. In one embodiment, the magnetic relaxation properties of the probe are correlated with the first and second concentrations of the nucleic acid, thereby quantifying the binding of the paramagnetic metal ion to the nucleic acid.

In another aspect, the invention features a method of determining the effect of a first species on the binding of a second species to a nucleic acid including the steps of measuring a magnetic relaxation property of a probe in a first solution using nuclear magnetic resonance spectroscopy, wherein the first solution includes a first concentration of the first species, the nucleic acid, the second species that binds to the nucleic acid, a paramagnetic metal ion, and a probe; measuring the magnetic relaxation property of the probe in a second solution using nuclear magnetic resonance spectroscopy, wherein the second solution includes a second concentration of the first species, the nucleic acid, the second species, the paramagnetic metal ion, and the probe; and comparing the relaxation properties measured, wherein a difference in the relaxation properties indicates the inhibition of the binding of the second species to the nucleic acid. In one embodiment, the magnetic relaxation properties of the probe are correlated with the first and second concentrations of the first species, thereby quantifying the effect of the first species on the binding of the second species to the nucleic acid.

The invention also features a method of detecting the availability of a paramagnetic metal ion in a solution comprising a nucleic acid including the steps of providing a solution comprising the nucleic acid, a probe, and the paramagnetic metal ion; and measuring a magnetic relaxation property of the probe in the solution using nuclear magnetic resonance spectroscopy, wherein the magnitude of the magnetic property is indicative of the availability of the paramagnetic ion in the solution.

In various embodiments of the above aspects, the first (or second) concentration of a species or ion may be 0.0 μM. In addition, a second concentration may be lower or higher than a first concentration, and a second solution may be formed by the addition or removal of species or ions from the first solution. Exemplary species include metal ions (e.g., $Mg^{2+}$) and candidate therapeutic agents (e.g., proteins, peptides, or fragments thereof). Desirably a candidate therapeutic agent is selected from a molecular library (e.g., a combinatorial library). The nucleic acid may be RNA or DNA and may also be double-stranded or single stranded. Exemplary paramagnetic metal ion include, without limitation, $Mn^{2+}$, $Fe^{2+}$, $Fe^{3+}$, $Co^{2+}$, $Ni^{2+}$, and a lanthanide ion. In other embodiments, the paramagnetic ion is bound to the nucleic acid. Desirably, the probe includes an X—H bond, wherein X is an NMR-active nucleus. In desirable embodiments, X is $^{31}P$, such as in methylphosphite or ethylphosphite. The probe may also be an alkylphosphonite, e.g., ethylphosphonite.

In addition, the magnetic relaxation properties of X may be indirectly detected using X edited, $^1H$ detected NMR spectroscopy. In various embodiments, the magnetic relaxation property is the $T_2$ relaxation of a nucleus of the probe. Desirably, the measuring of said magnetic relaxation properties of X proceeds by the steps of using a pulse sequence to transfer coherent magnetization originating on the $^1H$ nucleus to the X nucleus by Insensitive Nuclei Enhanced by Polarization Transfer (INEPT) techniques prior to a $T_2$ delay; providing a $T_2$ delay; and transferring the remaining coherence back to the $^1H$ nucleus for detection using a reverse INEPT series of pulses.

In another aspect, the invention features a kit for screening for species that bind to or inhibit binding to nucleic acids including a nucleic acid, a paramagnetic metal ion, and a probe, as described herein. The kit may further include an NMR spectrometer.

By "probe" is meant any molecule or species having at least one NMR active nucleus that undergoes a significant increase in transverse relaxation time ($T_2$) when in a solution containing a paramagnetic metal ion. Examples of NMR-active nuclei include, but are not limited to, $^1H$, $^{13}C$, $^{31}P$, $^5N$, $^{17}O$, and $^{19}F$ (see Yoder, C. H., et al. *Introduction to Multinuclear NMR*, Cummings:Menlo Park 1987, pp 317–319). Desirable probes include those that contain X—H bonds, where X is a non-hydrogen NMR-active nucleus. More desirably the probes contain P—H bonds. Particularly desirable probes are methylphosphite and ethylphosphonite. Other suitable probes contain only one NMR-active nucleus of an element other than hydrogen, e.g., $^{15}N$ or $^{31}P$.

By "species" is meant a molecule, atom, radical, ion, or metal ion. Desirable species include, but are not limited to, members of molecular libraries, inorganic compounds, synthetic molecules, natural products, antibiotics, drugs, drug candidates, derivatives of natural products, proteins, peptides, fragments of proteins, and $Mg^{2+}$.

By "nucleic acid" is meant substituted or unsubstituted RNA or DNA. Desirable nucleic acids are RNA molecules.

By "NMR-active nucleus" is meant a nucleus having a non-zero net nuclear spin.

By "biopolymer" or "biological polymer" is meant a protein, polypeptide, nucleic acid, or polysaccharide. The biopolymer may include naturally occurring components or synthetically modified components. In desirable embodiments, the biopolymer is a nucleic acid.

By "candidate therapeutic agent" is meant a chemical species that is identified by an assay as potentially having therapeutic efficacy for a specified condition. Exemplary candidate therapeutic agents include, without limitaion, natural and synthetic organic compounds, natural or synthetic inorganic compounds, natural or synthetic peptides or polypeptides, and nucleic acids.

By "bound to the nucleic acid" is meant coordinated to the nucleic acid and not free in solution.

By "availability" of species in solution is meant the ability of a probe to interact with the species to an extent that a magnetic property of the probe is altered. Species free in solution have a greater availability than those coordinated to a nucleic acid.

Other features and advantages of the invention will be apparent from the following description and the claims.

DETAILED DESCRIPTION OF THE INVENTION

Figure 1:
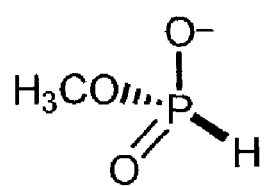
FIGS. 1A and 1B are schematic representations of chemical structures of methylphosphite (MeOPH) and ethylphosphonite (EtPH), respectively.
Figure 1:
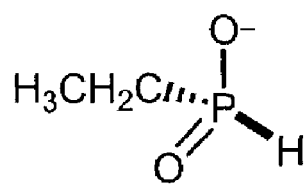

The invention features methods for detecting binding or inhibition of binding of a species to a biopolymer, e.g., a nucleic acid. Certain chemical species can be used as probes for studying metal coordination by such a biopolymer. The presence of paramagnetic metal ions affects the magnetic relaxation properties of nuclei in these probes as measured, for example, by NMR. The accessibility of paramagnetic metal ions to the probe in solution correlates with the magnitude of these effects on magnetic relaxation.

Certain biopolymers bind metal ions in solution. The addition or removal of species that affect the quantity of metal ions bound to a biopolymer, e.g., a nucleic acid, can be studied using a suitable probe. Methods based on this phenomenon can be used to study, for example, binding of metal ions directly to nucleic acids, species that bind to nucleic acids and displace metal ions, and species that inhibit the binding of other species to nucleic acids. The methods may also be used to study species that expose or conceal metal ions bound to biopolymers to allow or prevent interaction with a probe species, respectively.

Paramagnetic Metal Ions

Metal ions bound in vivo to biopolymers can usually be replaced with paramagnetic metal ions. For example, magnesium ions ($Mg^{2+}$) are normally found in vivo in nucleic acid complexes and can usually be replaced with, for example, manganous ion ($Mn^{2+}$). Ions such as $Mn^{2+}$ often support the structural and reactivity requirements of nucleic acids and their complexes for processing and binding proteins. The chemistry of $Mn^{2+}$ also closely approximates that of $Mg^{2+}$. These two cations show similar preferences for six coordination sites and have similar bond energies and Lewis acidities. While the chemistry of $Mn^{2+}$ and $Mg^{2+}$ are similar, their magnetic properties are very different. $Mg^{2+}$ is diamagnetic (having no unpaired electrons), and $Mn^{2+}$ is paramagnetic (containing five unpaired electrons). Additional exemplary paramagnetic ions that are useful in the methods described herein include, without limitation, $Fe^{2+}$, $Fe^{3+}$, $Co^{2+}$, $Ni^{2+}$, or a lanthanide ion.

Probes

Magnetic resonances of certain nuclei can be highly sensitive to paramagnetic ions, and compounds containing these NMR-active nuclei can be used as probes for the presence of paramagnetic metal ions. For example, the $^{31}$P nuclei of certain anionic materials including methylphosphite are remarkably sensitive to magnetic $T_2$ relaxation by $Mn(H_2O)_6^{2+}$ (or free $Mn^{2+}$). Changes in the $^{31}P$ NMR transverse relaxation rates of MeOPH can be used, for example, to detect and quantify the concentration of $Mn^{2+}$ in aqueous solutions at concentrations below 1 µM.

Previous work has measured magnetic relaxation of molecules in close proximity to paramagnetic metal ions, but significant differences exist between the methods of this invention and those of the prior art. In previous approaches, it is the magnetic resonances of the biopolymers, e.g., nucleic acids, themselves that are observed. Methods that center on measuring the effect of metal ions have on the resonances of the biopolymers are unlikely to develop into reasonable screens for drug activity. Such a method would require that the biopolymers be present in the solutions at concentrations of hundreds of µM or above. Since the analyte must also be present at this concentration, the effects of weak interactions ($K_d$~100 µM) cannot be distinguished from those of stronger interactions. Since compounds that only weakly interact are unlikely to make good drug candidates, and weak binders cannot be differentiated from stronger binders, these methods are of limited use. The concentration limitations also mean that drugs with lower solubilities cannot be studied by these methods. Since the methods of the present invention observe the resonances of a probe, they are not limited to working with high concentrations of biological species and can be used to screen for drug hits at more physiological conditions.

Another limitation on methods where macromolecular resonances are observed arises from the spectral overlap of these resonances: resolution and assignment of these resonances would require multi-dimensional spectroscopy of isotopically labeled samples. An additional benefit arises for the methods described herein since they do not require the assignment of the macromolecular resonance chemical shifts. Macromolecules have many nuclei of a given element, e.g., H, C, N, or P, that may be present in chemical environments that only slightly differ. Since small differences in chemical environment give rise to small differences in chemical shift, the precise assignment of one nucleus out of the many similar nuclei is difficult.

The probes described herein form a complex with the paramagnetic metal ions. This complex is weakly bound relative to complexes of the metal ions and nucleic acids. Complexation of the probe to the metal ion affects the magnetic relaxation properties of the probe. To achieve the maximum sensitivity in methods that measure metal ion availability in solution, interactions between the probe are paramagnetic metal ion are desirable minimized when the ion is bound to a biopolymer. For example, one method to minimize the interaction of the probe with metal ions bound to nucleic acids is to make the probe anionic. Since the metal ion is sequestered by a poly-anionic nucleic acid, the overall charge will be highly negative and repel the anionic probe ion. Thus, changes in the magnetic relaxation properties by the sequestered metal ion are not observed. If association with monovalent cations neutralizes the anionic charge of the nucleic acid, then relaxation enhancement by the nucleic acid/$Mn^{2+}$ complex is possible. In methods that measure the accessibility of a metal ion bound to a biopolymer, however, the probe desirably interacts with the bound metal. For example, the probe may be of the opposite charge to the biopolymer, or it may be neutral.

Exemplary probes are shown in FIG. 1. These probes have at least one P—H moiety and at least one terminal P—O moiety, examples include alkyl phosphite anions (e.g., methylphosphite, MeOPH, and ethylphosphite, EtOPH) and phosphonite anions (e.g., ethylphosphonite, EtPH). These probe ions are far more sensitive to metal ions than the water $^1H$ resonance and have the advantage over fluoride of allowing $^1H$ detection with isotope editing (Dwek, R. A. *Nuclear Magnetic Resonance in Biochemistry* Clarendon: Oxford 1973).

NMR

Nuclear magnetic resonance (NMR) spectroscopy is a widely used technique to study chemical and structural properties of species. The ability to detect magnetic relaxation rates, e.g., from $T_1$ and $T_2$ relaxations, provides a route to probe the environment of a particular nucleus.

Figure 2:
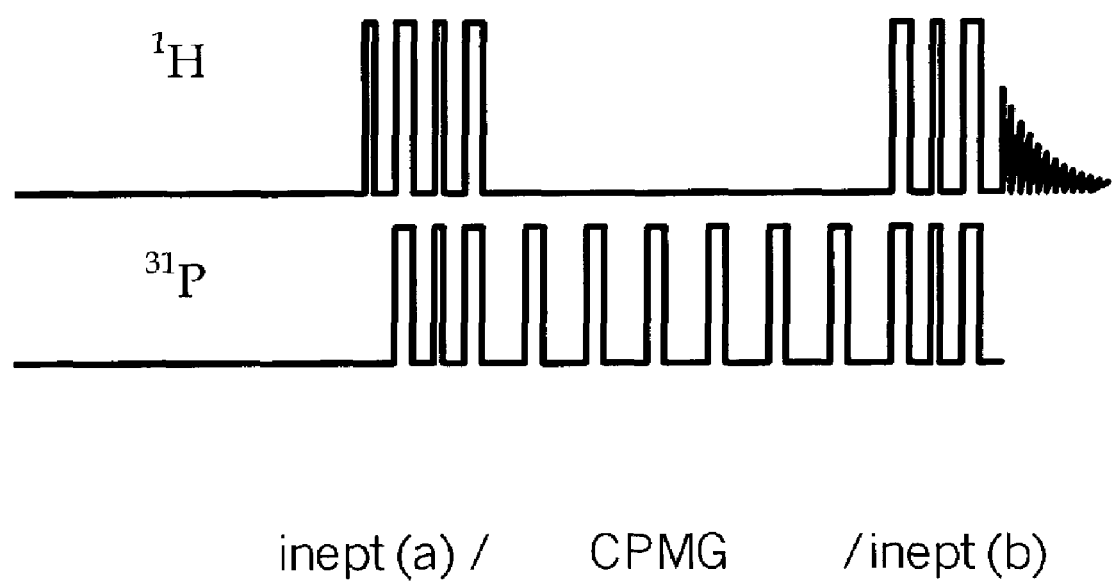
FIG. 2 is a schematic representation of one-dimensional pulse sequences for measuring $^{31}P$ $T_2$ values using $^1H$ detection. Broad and narrow bars represent 180- and 90-degree pulses, respectively.

For probes containing X—H bonds, the $T_2$ relaxation of the X nucleus can be monitored using $^1H$ detection and isotope editing. For example, a pulse sequence for a one-dimensional NMR experiment used to determine changes in $^{31}P$ $T_2$ of phosphites or phosphonites with indirect detection is shown in FIG. 2. In this example, coherent magnetization originating on the $^1H$ is transferred to the $^{31}P$ via inept sequence (a). The sample is pulsed with a series of 180-degree phosphorus re-focusing pulses (during the CPMG train), and magnetization is transferred back to the $^1H$ nucleus for detection (inept sequence (b)). Delays between pulses in the two inept sequences are set to 1/4J. Pulse phases are those described by Farrow et al., for a $^{15}N$ $T_2$ correlation experiment (Farrow, N. A. et al. *Biochemistry*, 1994, 33:5984–6003). The number of 180-degree phosphorus refocusing pulses during the CPMG portion of the sequence and the delay between these pulses can be adjusted to alter the total time in the CPMG train. During this time (which is called the $T_2$ time) transverse relaxation of the $^{31}P$ nucleus occurs, leading to a diminution of the intensity (i) of the observed signal. For example, the effect of variations in $T_2$ time on the intensity of the phosphite $^1H$ signal of EtOPH in a solution containing 5 µM $Mn^{2+}$ is presented in FIG. 3. In this example, the delay between $^{31}P$ 180-degree pulses was held fixed at 200 µs, and the number of pulses increased as the length of the CPMG pulse train increased. For example, the shortest time corresponds to 8 CPMG pulses, and the longest time corresponds to 160 pulses. The transverse relaxation time of the $^{31}P$ nucleus of the probe under these conditions is equal to the magnitude of the slope of the plot. While this particular example is for $^{31}P$ nuclei, the technique is generally applicable to other NMR-active nuclei X that form strong X—H bonds.

The sensitivity of the technique depends, e.g., on the reproducibility of the instrumentation, sample variability, and any paramagnetic impurities or dissolved oxygen present in the sample. The sensitivity also depends strongly on the charge of the biopolymer. For example for RNA in low salt solutions, changes in $Mn^{2+}$ concentration of ~300 nM are detected with suitable reproducibility.

Applications

The methods of the present invention can be used to study the relative or absolute increase or decrease in the accessibility of metal ions in solution.

The ability to detect and quantify the concentration of free paramagnetic metal ions in solution provides methods, for example, to screen a series of drug candidates for species that bind to biopolymers, e.g., a nucleic acid, or inhibit the binding of other species to biopolymers, to determine the stoichiometry of metal ions binding to biopolymers, or to determine relative or absolute affinities of species binding to biopolymers. The ability to detect and quantify the accessibility of a metal ion bound to a biopolymer provides methods, for example, to screen for ligands that bind or inhibit the binding of species to the metal or biopolymer.

In one embodiment, species that bind to nucleic acids displace bound paramagnetic metal ions and cause an increase in the concentration of paramagnetic metal ions free in solution. This increase in concentration is measured, for example, by NMR as an increase in the $T_2$ relaxation rate of nuclei in a probe. The $T_2$ relaxation rates are then correlated with the concentration of species that binds to nucleic acid to detect or quantify the amount of paramagnetic metal ions freed upon binding of the species to nucleic acid. The species that binds the nucleic acid may be, e.g., a synthetic organic molecule, a peptide, or a protein.

In another embodiment, nucleic acid is added to a solution of free paramagnetic metal ions. The ions then bind to the nucleic acid. This binding is measured, for example, by NMR as a decrease in the $T_2$ relaxation rate of nuclei in a probe. The change in the rate of relaxation of nuclei in the probe is then correlated with the concentration of nucleic acid to detect or quantify the binding of paramagnetic metal ions to the nucleic acid.

In still another embodiment, a species that potentially inhibits the binding of other species, e.g., a protein, to nucleic acids is added to a solution containing a species bound to a nucleic acid and paramagnetic metal ions. Desirable proteins for binding inhibition include, without limitation, the Hu antigens and AUF1 (Wilson, G. M. et al. *J. Biol. Chem.* 2001, 276:8695–8704). The inhibiting species reduces the concentration of the other species bound to the nucleic acid, which allows paramagnetic metal ions to bind to the nucleic acid. The binding of paramagnetic metal ions to the nucleic acid reduces the concentration free in solution. The inhibition of binding of the species to the nucleic acid is measured, for example, by NMR as a decrease in the $T_2$ relaxation rate of nuclei in a probe caused by the reduced concentration of metal ions in solution. The change in the rate of relaxation of the nuclei in the probe is then correlated with the concentration of the inhibiting species to detect or quantify the inhibition of species binding to nucleic acid.

EXAMPLES

The following examples are provided merely to illustrate various features and other details of the invention and should not be construed as limiting.

In Examples 1–15, the effects of RNA on equilibrium concentrations of $Mn^{2+}$ are determined using a phosphite probe ion (either Methyl phosphite, MeOPH, or Ethyl phosphite, EtOPH). Typically, samples of MeOPH were prepared at (5–10 mM) in PIPES buffer (5–10 mM), which is known not to interfere with metal ion availability (Kandegedara A. et al. *Anal. Chem.* 1999, 71:3140:3144). Aliquots of stock solutions were evaporated in vacuo and reconstituted in $D_2O$ (all experiments used $D_2O$ as solvent). Samples were treated with aliquots of $Mn^{2+}$ in the presence and in the absence of the RNA of interest.

Example 1

Synthesis of MeOPH and EtOPH

MeOPH was prepared by partial hydrolysis of dimethyl phosphite in aqueous base. Dimethyl phosphite (for MeOPH) or diethyl phosphite (for EtOPH) (Aldrich) was dissolved in deionized water, and the resulting solution was neutralized by addition of an equivalent of either sodium hydroxide (to prepare the sodium salt) or potassium hydroxide (to prepare the potassium salt). The progress of the reaction was monitored using a pH meter. The rate of addition was such that the temperature of the solution was not allowed to exceed ~60° C. On a gram scale (~2 M concentration), the process is complete in ~5 minutes. Aliquots of the sample were then evaporated in vacuo to give a colorless powder that could be dissolved into $D_2O$ for spectroscopic studies. The phosphorus bound proton did not exchange readily with those of the solvent.

Example 2

Synthesis of EtPH

EtPH was prepared by hydrolysis of ethyl-dichloro-phosphine. To a beaker of deionized water in an ice bath was added the contents of a one-gram ampoule of ethyl-dichloro-phosphine with stirring. A vigorous exothermic reaction ensued. The sample was neutralized with aqueous base, and aliquots were evaporated in vacuo.

Example 3

Measurement of $T_2$ Relaxation Rates with NMR Spectroscopy

Figure 3:
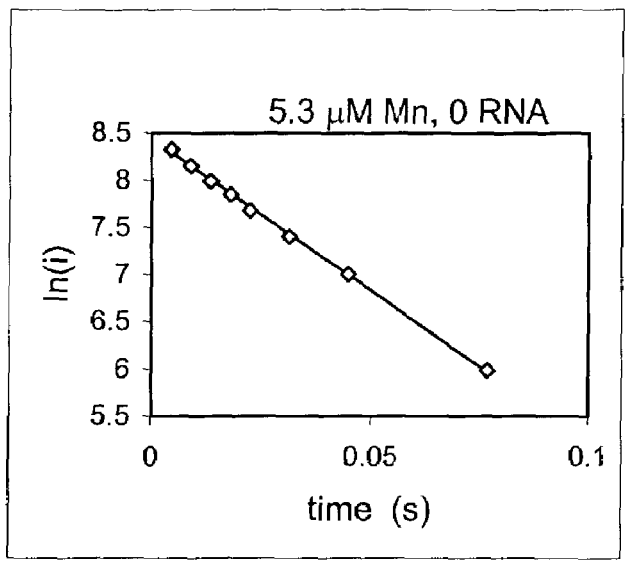
FIG. 3 is a graph showing the intensity (i) of the $^1$H signal of ethylphosphite (EtOPH) obtained using the pulse sequence of FIG. 2 as a function of the length of the CPMG pulse train.

The $^{31}P$ $T_2$ was measured for each sample by varying the length (number of pulses) of the CPMG portion of the pulse sequence in FIG. 2 and determining the effect of this change on the intensity (i) of the signals. Plots of ln(i) versus time (as seen in FIG. 3) were linear with a slope equal to the negative of the $^{31}P$ $T_2$. The d1 delay was typically 5 to 20 seconds, and delays in the inept and reverse inept parts of the sequence were set to a value equal to 1/4J, where J is the $^1H$—$^{31}P$ coupling constant. Delays between pulses in the CPMG train varied from 50 to 500 microseconds.

Example 4

$Mn^{2+}$ Binding Properties of a 38 Nucleotide RNA

A TNF-α mRNA construct binds divalent metal ions in a way that poly-U does not (Wilson, G. M. et al. *J. Biol. Chem.* 2001, 276:8695–8704). Complex formation between the RNA binding protein AUF1 and its target RNA is inhibited by $Mg^{2+}$, and RNA binds $Ca^{2+}$ and $Mn^{2+}$ as well as $Mg^{2+}$. These results indicate that metal ions are released from specific sites on RNA when bound to AUF1.

Figure 4:
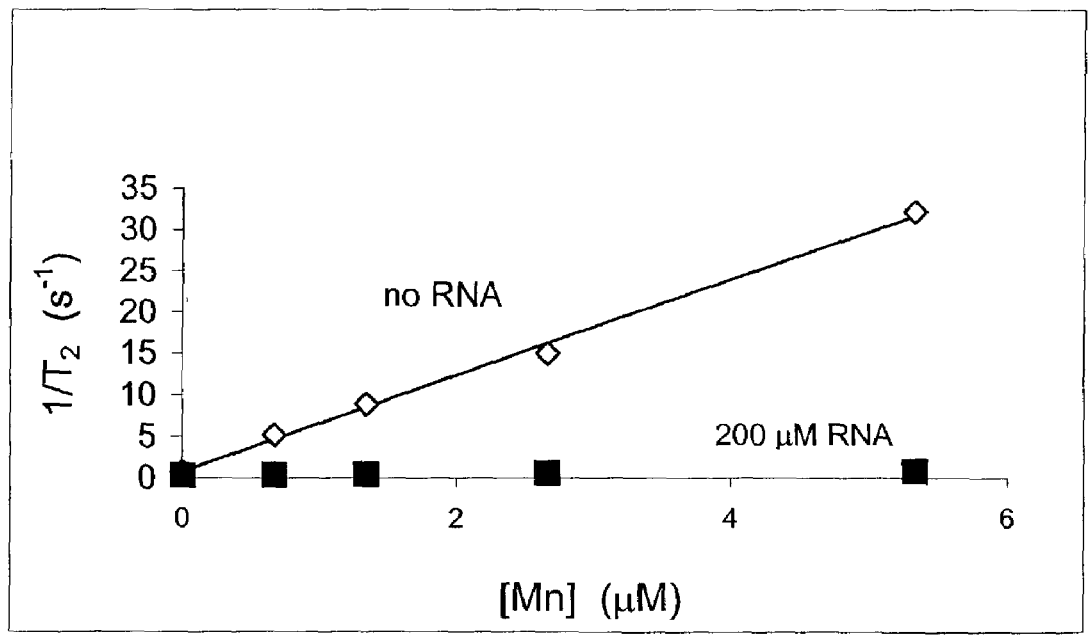
FIG. 4 is a graph showing the inverse of the $T_2$ relaxation time ($1/T_2$) of EtOPH $^{31}$P with and without RNA present as a function of the concentration of $Mn^{2+}$.

A solution of EtOPH (5 mM) in $D_2O$ was prepared and aliquots were treated with aliquots of $Mn^{2+}$. Similar samples were prepared but with a 38 nt ARE RNA construct at a concentration of 200 μM. The sequence of this RNA was identical to that reported (Wilson, G. M. et al. *J. Biol. Chem.* 2001, 276:8695–8704) to bind divalent metal ions. In the absence of the RNA, the measured value of the $^{31}P$ $T_2$, obtained as described in Example 3, decreased with the addition of metal ion. When the reciprocal of $T_2$ of the $^{31}P$ nucleus was plotted versus $Mn^{2+}$ concentration, a linear correlation was obtained (open diamonds in FIG. 4). In contrast, the $^{31}P$ $T_2$ of the probe was not measurably affected by the same level of $Mn^{2+}$ in the presence of the RNA (filled squares in FIG. 4). These results indicated that $Mn^{2+}$ was effectively sequestered by the RNA and that, once sequestered, $Mn^{2+}$ ions did not affect the relaxation properties of the probe ion.

Example 5

Determining the Affinity of the RNA for $Mn^{2+}$

Figure 5:
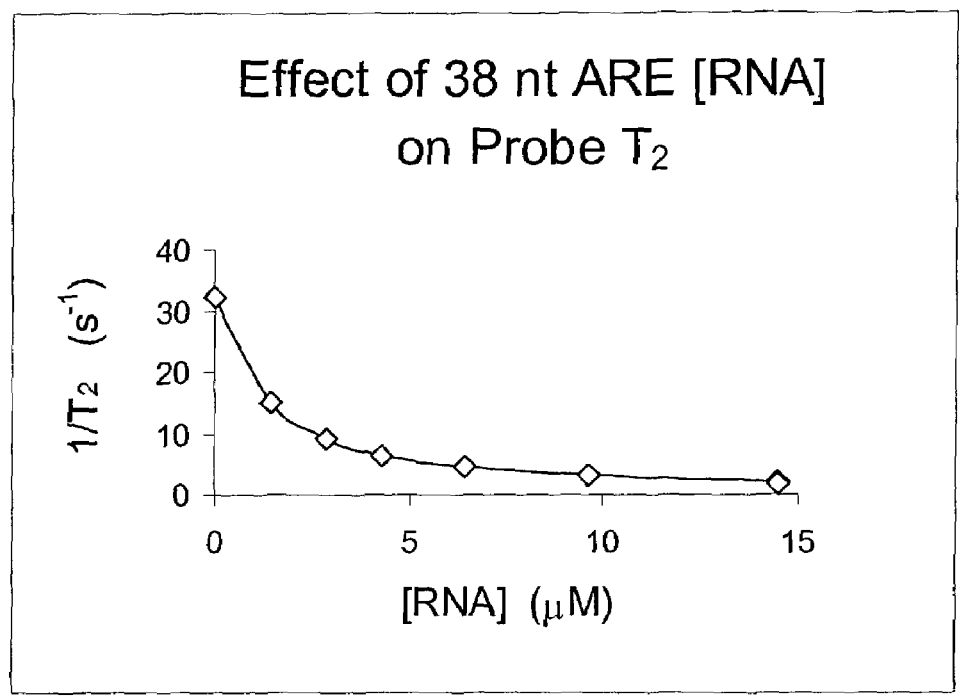
FIG. 5 is a graph showing the inverse of the $T_2$ relaxation time ($1/T_2$) of EtOPH $^{31}$P in the presence of 5.3 µM $Mn^{2+}$ as a function of RNA concentration.

Example 4 demonstrated that the affinity of the 38 nt ARE construct for $Mn^{2+}$ was sufficient to reduce the level of free $Mn^{2+}$ from 5.3 to less than 1 µM. To estimate the binding affinity of the nucleic acid for $Mn^{2+}$, samples containing the probe ion (EtOPH, 5 mM) and $Mn^{2+}$ (5.3 µM) were treated with aliquots of the RNA construct (final concentrations of 0, 1.4, 2.9, 4, 6, 10, 14, 58, and 232 µM), and the values of the probe ion $^{31}P\ T_2$ were measured for each sample as in Example 3. A plot of reciprocal $T_2$ versus RNA concentration (FIG. 5) shows that metal ion sequestration was efficient for this sequence well below 10 µM. This figure also shows that more than one metal ion was bound per molecule of nucleic acid under these conditions.

Example 6

Determining the Affinity of a Drug Candidate for RNA

Figure 6:
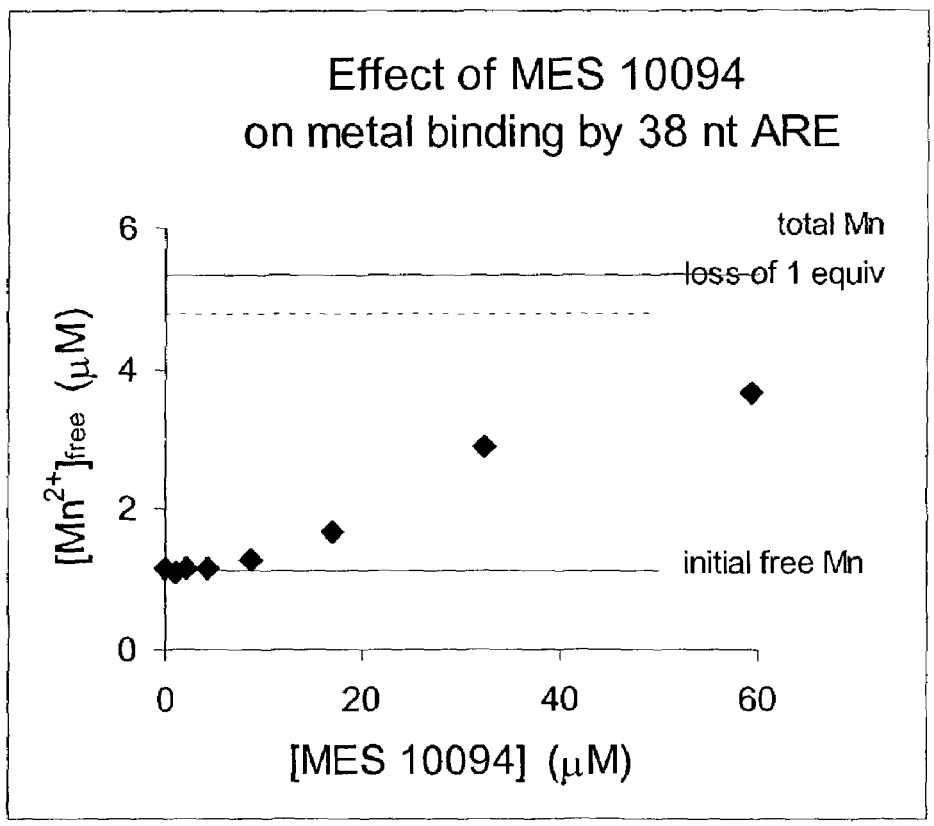
FIG. 6 is a graph showing the concentration of free $Mn^{2+}$ in the presence of 3.6 µM of RNA as a function of the concentration of the nucleic acid binding compound MES 10094.

To determine the affinity of an RNA-binding drug candidate, MES10094, disclosed in U.S. application Ser. No. 10/117,955 filed on Apr. 8, 2002, for the 38 nt RNA, a sample containing $Mn^{2+}$ (5.3 µM), probe (5 mM), and RNA (3.6 µM) was treated with a concentrated solution of MES 10094. The effect of increasing concentration of the drug lead on the $^{31}P\ T_2$, measured as in Example 3, is presented in FIG. 6. This figure clearly shows that addition of MES 10094 resulted in a pronounced increase in the rate of probe ion $^{31}P\ T_2$ relaxation. This result was consistent with the drug candidate displacing a fraction of the bound $Mn^{2+}$ from the RNA. The data in FIG. 6 indicated that the $K_D$ for metal displacement by MES 10094 under these conditions was on the order of 30 µM, which was consistent with values for inhibition of AUF1 binding to the RNA by MES 10094.

Example 7

Determining the Affinity of a Drug Candidate for a Species that Binds to RNA To determine the affinity of a drug candidate for an RNA-binding species, e.g., a protein, a sample containing $Mn^{2+}$ (5.3 µM), probe (5 mM), RNA-binding species (over a concentration range that spans an order of magnitude greater than and less than the expected $K_d$), and RNA (3.6 µM) is treated with a drug candidate. The effect of increasing concentration of the drug lead on the $^{31}P\ T_2$, measured as in Example 3, is then determined. The addition of a successful drug lead results in a pronounced decrease in the rate of probe ion $^{31}P\ T_2$ relaxation. This result is consistent with the drug candidate preventing the binding of the RNA-binding species and allowing a fraction of the free $Mn^{2+}$ to bind to the RNA. The $K_D$ for binding to the RNA-binding species under these conditions is determined from curve fitting the data.

Example 8

Screening a Molecular Library for Drug Candidates

Species in a molecular library are screened to determine drug candidates that bind to RNA or inhibit binding of other species to RNA. Screening for RNA-binding candidates proceeds as in Example 6, and screening for candidates that inhibit binding of other species to RNA proceeds as in Example 7. Several compounds may be screened at once. If a mixture contains a drug candidate, the individual species are then tested to determine the active species.

Example 9

Determining Non-Sequence Specific Association of Metals Ions with RNA

Figure 7:
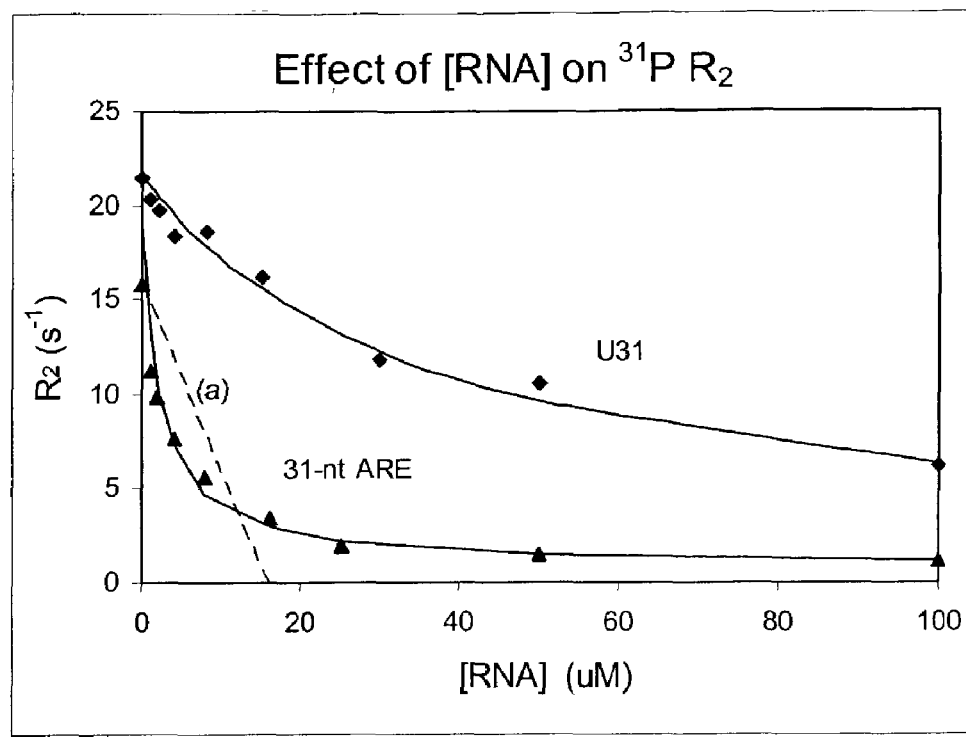
FIG. 7 is a graph showing the effect of RNA concentration on paramagnetic $T_2$ relaxation enhancement by $Mn^{2+}$.

To establish the effects of non-specific interactions, metal ion association with a 31-nucleotide poly-U RNA ($U_{31}$) was compared to association with a 31 nucleotide ARE construct. The effects of these two 31-nucleotide RNA constructs on the availability of $Mn^{2+}$ in low salt (~12 mM $Na^+$) solutions of 5 mM PIPES, pH 7.2, as measured in Example 3, are shown in FIG. 7. The effects of $U_{31}$ are represented by diamonds while those of the 31-nt ARE construct are represented by triangles. This figure clearly demonstrates the base specific nature of metal binding. Solid lines represent behavior predicted by a model wherein a single binding site existed with $K_d$ values of 38 (upper line) and 2.7 µM (lower line). Dashed line (a) represents behavior predicted for a model where the ARE construct bound a single metal ion with high affinity.

This system was used to investigate the effects of added electrolytes on metal binding. While added sodium chloride had little effect on $Mn^{2+}$ binding by the 31-nt ARE, addition of 100-mM $Na^+$ resulted in negation of the effects of the $U_{31}$ construct. This result shows that $Na^+$ competes effectively with $Mn^{2+}$ for association with the $U_{31}$ construct but not with the ARE construct. The differences between the behaviors of $U_{31}$ and the ARE construct indicate that the ARE construct has specific binding sites for divalent cations, such as $Mn^{2+}$. In the higher salt solution, 50 µM RNA had about half the effect on magnetic relaxation than it did in the lower salt solution (data not shown).

Example 10

Titration of $Mn^{2+}$ with A-Site RNA under Low Salt Conditions

Figure 8:
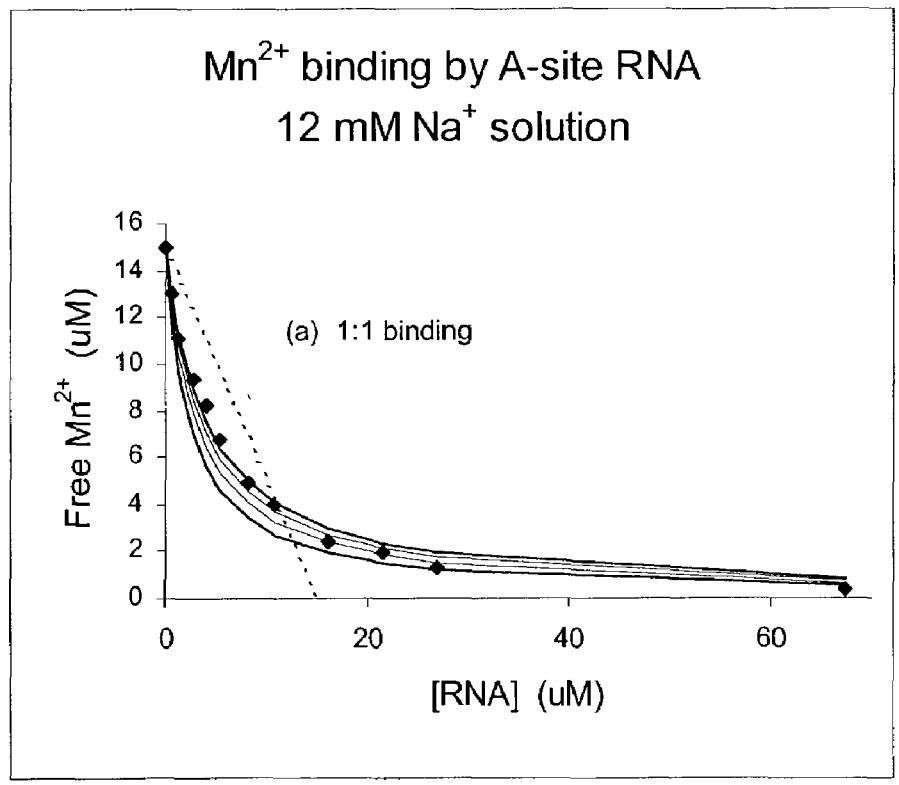
FIG. 8 is a graph showing the effect of a 27-nt A-site RNA construct on probe ion relaxation enhancement by $Mn^{2+}$.

In solutions containing 5 mM each of the sodium salts of MeOPH and PIPES buffer (pH 7.2), the concentration of sodium ion is calculated to be ~12.5 mM. Addition of a 27-nt A-site construct to a solution of $Mn^{2+}$ under these conditions caused the uptake of multiple $Mn^{2+}$ ions per molecule of RNA, as measured as in Example 3. The data are presented in FIG. 8. The behavior predicted for tight binding in a 1:1 stoichiometry is presented as dashed line (a). The series of unbroken curves illustrates the behavior predicted by binding different numbers of metal ions at assumed values of $K_d$. In this model, all sites were assumed to have the same $K_d$ and behave independently of whether other sites were occupied. The lowest curve represents binding of four $Mn^{2+}$ ions with a $K_d$ of 4.6 µM. The highest curve represents binding of 8 $Mn^{2+}$ ions with a $K_d$ of 32 µM.

Example 11

Displacement of Metal Ions from the A-Site by Neomycin

Figure 9:
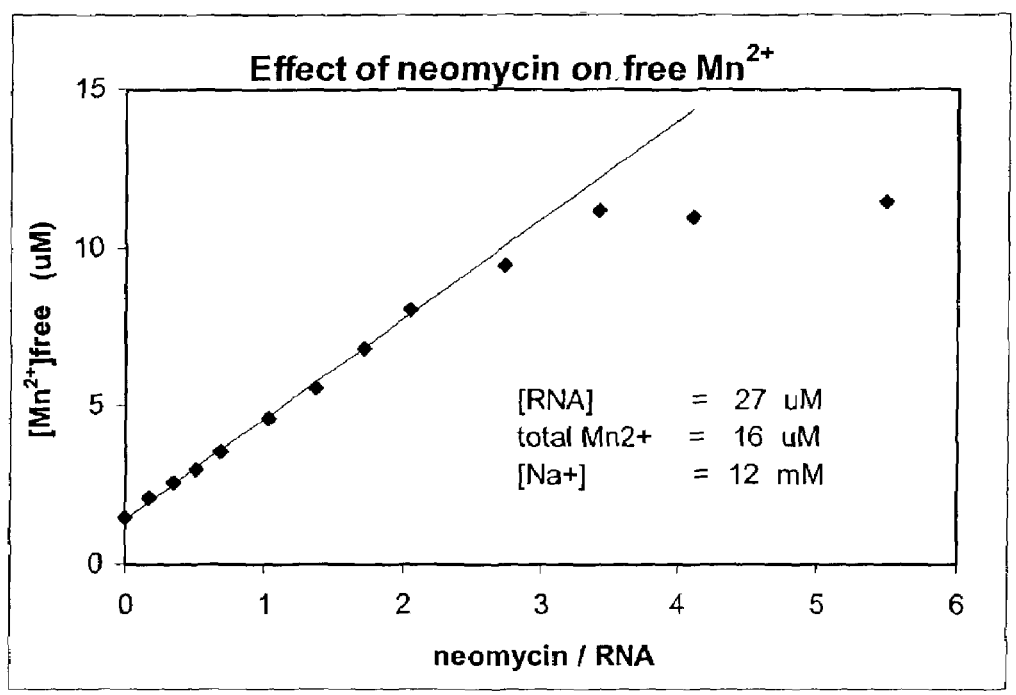
FIG. 9 is a graph showing the displacement of bound $Mn^{2+}$ from a 27-nt A-site RNA construct by neomycin.

FIG. 9 shows the effect of titration of a solution of a 27-nt A-site RNA construct (27 µM), complexed with $Mn^{2+}$ (16

μM), with neomycin, measured as in Example 3. Data in this figure show that metal ions were displaced by addition of the aminoglycoside drug, neomycin, as was suggested by Mikkelsen et al (Mikkelsen, N. E. et al. *Nature Struct. Biol.* 2001, 8:510–514). The data shown in FIG. 9 were most consistent with a model where three neomycin molecules were bound to each RNA molecule with subsequent release of $Mn^{2+}$. Release of $Mn^{2+}$ resulted in an increase in the relaxation rate of the probe ion phosphorus nucleus.

Example 12

Figure 10:
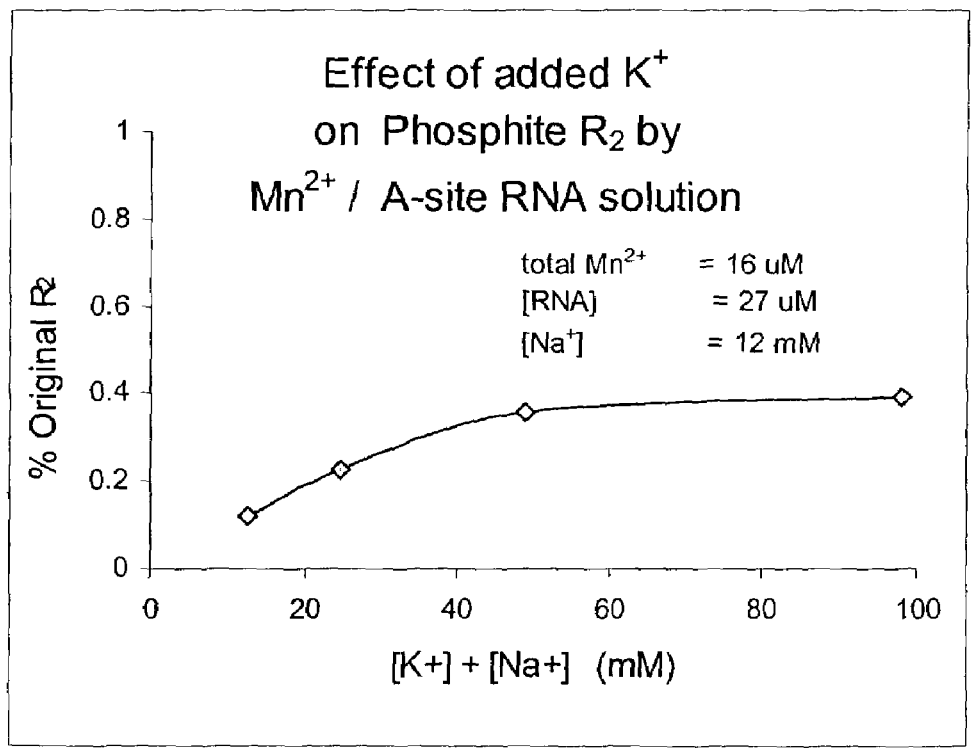
FIG. 10 is a graph showing the effect of electrolyte concentration on relaxation enhancement, expressed as a fraction of enhancement expected in the absence of RNA, in solutions of a 27-nt A-site RNA construct and $Mn^{2+}$.

The Effects of Electrolytes on Magnetic Relaxation in Solutions of $Mn^{2+}$ and RNA The effect of $K^+$ ion concentration on relaxation enhancement is shown in FIG. 10. While the addition of KCl solution resulted in an initial increase in relaxation enhancement, measured as in Example 3, after the concentration of monovalent ions exceeds about 40 mM, addition of more KCl had little effect. This apparent saturation effect could have one of two possible origins: the monovalent ions were only able to displace some percentage of the divalent ions from their binding sites, or at sufficiently high concentrations, monovalent ions associated with the RNA, neutralizing its negative charge. If the latter occurs, then relaxation of the phosphorous nucleus by the coordinated $Mn^{2+}$ becomes possible.

Example 13

Determining the Effects of Potassium Ion on the Shapes of Titration Curves

Figure 11:
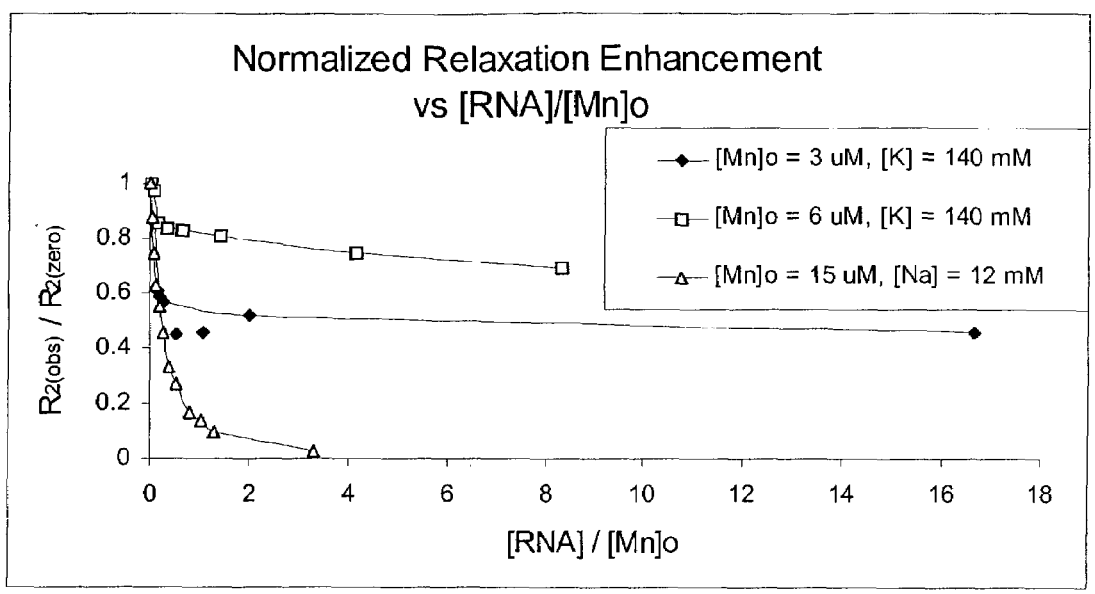
FIG. 11 is a graph showing $Mn^{2+}$ binding by a 27-nt A-site RNA construct under different salt concentrations.

The effects of 140 mM $K^+$ on the curves obtained when solutions of $Mn^{2+}$ are titrated with the 27-nt A-site construct are presented in FIG. 11. In contrast to the behavior observed in low salt, titrations in 140 mM $K^+$ did not result in complete loss of relaxation enhancement, measured as in Example 3. A comparison of titrations run in 3 and 6 μM $Mn^{2+}$ solutions shows that impurities introduced with the KCl or the buffer were not responsible for the residual relaxation enhancement. These results were most consistent with a model where association of monovalent ions with the A-site RNA resulted in a significant decrease in charge density, and as a result, the probe ion was able to contact the $Mn^{2+}$ while bound to the nucleic acid.

Example 14

Determining the Number of High Affinity Metal Binding Positions on RNA

Under suitable conditions, it will be possible to determine the number of metal ions that are tightly bound by a given nucleic acid. Titration of a solution of the nucleic acid into a solution containing the paramagnetic metal ion and the probe ion will result in a decrease in the availability of the metal with the result that it will decrease the rate of $T_2$ relaxation of the probe nuclei, measured as in Example 3. The change in free metal concentration can be determined from the change in the relaxation rate. The following relationship applies:

$$1/T_{2,a} - 1/T_{2,b} = k\{[M]_a - [M]_b\}$$

where the subscripts a and b refer to solutions a and b, and k is a constant. For $Mn^{2+}$ solutions k is equal to the second order rate constant for reaction with the probe ion, for MeOPH, this value is $5.8 \times 10^6$ $M^{-1}s^{-1}$. Plotting the concentration of added nucleic acid versus the change in metal concentration will give a curve where the initial slope is equal to the stoichiometric ratio of metal ions bound per nucleic acid. To prevent interference from non-specific metal binding, these experiments may be performed at varying ionic strengths using an inert electrolyte such as ammonium acetate.

Example 15

Developing Structure Activity Relationships (SAR's) from Affinity Data

Using affinity data, structure activity relationships are developed to refine drug leads by established methods (Hajduik, P. J., et al. *Quarterly Rev. Biophys.* 1999, 32:211–240; Moore, J. M. *Current Opin. Biotech.*, 1999, 10:54–58).

Example 16

Displacement of $Mn^{2+}$ from RNA

Figure 12:
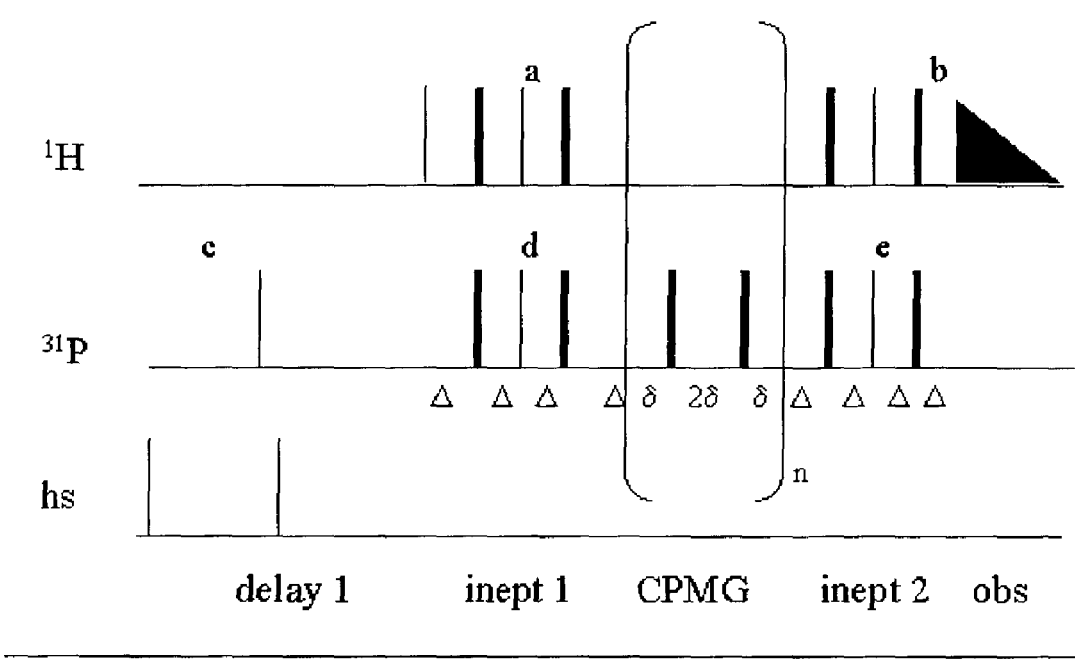
FIG. 12 is a schematic description of a one dimensional pulse sequence for measuring phosphite $^{31}$P $T_2$ values. Coherence originating on the phosphorus bound proton ($^1$H—P) nucleus is transferred to the $^{31}$P nucleus using a series of inept pulses. After a series of CPMG 180 degree refocusing pulses ($^{31}$P frequency), the remaining signal is returned to the $^1$H—P nucleus for detection using a second series of inept pulses. The transverse relaxation times ($T_2$) were determined from the slopes of the linear plots of log(i) versus t where i is the maximum intensity of the resonance, and t is the time between the two inept series of pulses (t=4nδ). Narrow and broad lines represent 90 and 180 degree pulses on the indicated channel. A 90 degree $^{31}$P pulse and two homospoil pulses are inserted into delay 1 to remove artifacts arising from residual magnetization remaining between transients. All pulse phases are zero unless noted otherwise. Delays in the inept 1 and inept 2 portion of the sequence (Δ) are equal to 1/4J. The delay between CPMG pulses (δ) was 4 ms. The $T_2$ delay was varied by changing the number of times through the CPMG cycle (n). Phase cycles were as follows: a=(1,1,1,1,3,3,3,3), b=(2), c=(3,3,3,3,3,3,3,3,1,1,1,1,1,1,1,1), d=(0,2), e=(0,0,2,2), and obs=(2,0,0,2,0,2,2,0).

NMR spectra were recorded on either a Varian Mercury 200 MHz, or a Bruker Avance DRX 500 MHz NMR spectrometer. Transverse relaxation rates ($R_2=1/T_2$) were measured indirectly by exploiting the strong scalar coupling between the phosphorus and the phosphorus bound hydrogen ($J_{HP}=630$ Hz). The one dimensional pulse sequence is described in FIG. 12.

RNA constructs were purchased from Dharmacon (Lafayette, Colo.) already gel purified and desalted. The samples were washed repeatedly, first with 1 M NaCl, and then with $H_2O$, using a centricon filtration device. Samples were subsequently lyophylized and reconstituted in $D_2O$ Prior to use. Neomycin b was purchased from Sigma (St. Louis, Mo.) and was used without further purification. The K+ salt of MeOPH was prepared by hydrolysis of $(MeO)_2P(H)O$ (Aldrich, St. Louis, Mo.) with KOH solution. The reaction was monitored by pH, and was evaporated to dryness in vacuo. Similarly, $K_2HPO_3$ was prepared by neutralization of phosphorus acid (Aldrich) with KOH. Samples were pure by $^1H$ and $^{31}P$ NMR and were used without further purification. The RSG1.2 Peptide (Tan, R.; Frankel, A. D., *Biochemistry* 1994, 33: 14579–14585) was prepared by Synpep, Inc (Dublin, Calif.), with a TAMRA label on the N-terminus. All NMR studies were performed in $D_2O$ using PIPES as a non-complexing ionic buffer (Yu, Q.; Kandegedara, A.; Xu, Y.; Rorabacher, D. B., *Ana.l Biochem.* 1997, 253: 50–56). The buffer was prepared as the $K^+$ salt by neutralization of the free acid with KOH.

Figure 13:
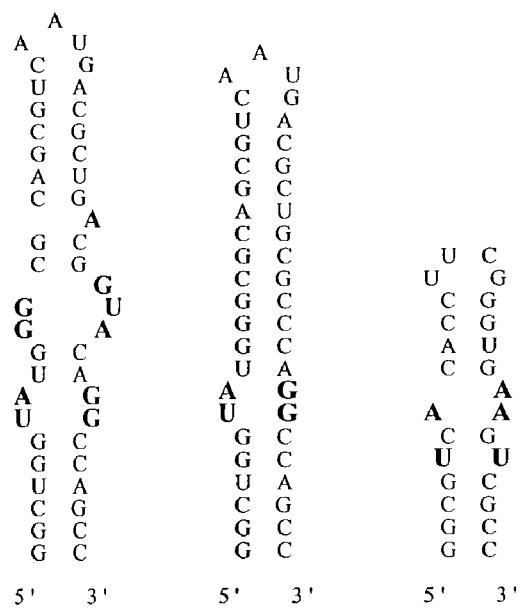
FIG. 13A is a schematic depiction of RRE1, RRE2, and A-site hairpin structures.
FIG. 13B is a schematic depiction of neomycin b.
FIG. 13C is a schematic depiction of RSG1.2.
Figure 13:
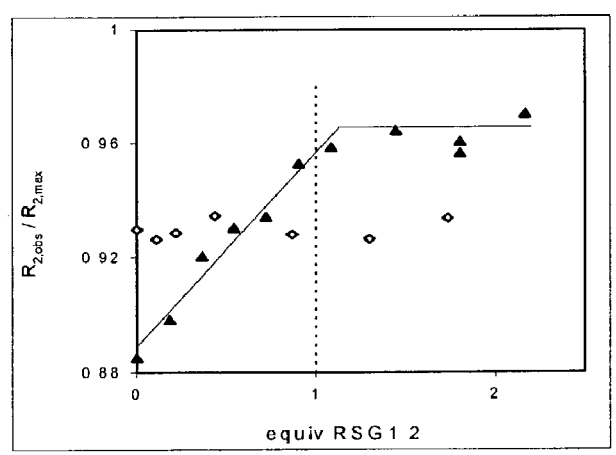

$Mn^{2+}$ binding by RNA constructs, and its displacement by either $K^+$ or $Mg^{2+}$. Samples containing MeOPH (5 mM) and PIPES buffer (5 mM, pH=7.2), and 3 μM $Mn^{2+}$ were titrated with each RNA. The $^{31}P$ transverse relaxation rates ($R_2=1/T_2$) of the probe in the resulting solutions were measured. Plots of $R_2$ versus [RNA] were prepared. The effects of $[K^+]$ and $[Mg^{2+}]$ on $Mn^{2+}$ binding were determined by titrating similar solutions containing buffer, MeOPH, $Mn^{2+}$ and one of the RNAs (10 to 30 μM) with solutions of either KCl or $MgCl_2$, and monitoring the relaxation rate of the probe as a function of cation concentration. The effects of $[K^+]$ were studied over the range of 12.5 to 150 mM (intercellular $K^+$ is reportedly 140 mM). $Mn^{2+}$ displacements from each of the hairpins by $Mg^{2+}$, neomycin b, and RSG1.2 were studied in the absence of added KCl and with sufficient KCl added to bring the total [K⁺] to 100 mM. The compounds employed in this example are shown in FIG. 13.

Displacement of $Mn^{2+}$ from RNA by RSG1.2, or neomycin b: Binding of RSG1.2 and neomycin b to each of the hairpins was studied at [RNA] between 20 and 30 µM, and again at [RNA]~3 µM. The higher concentration studies were performed in a manner identical to that described above for the $Mg^{2+}$ exchange reactions. For the low concentration studies, $HPO_3^{2-}$ (20 mM) was used as the probe ion. Reactions were run in 10 mM PIPES buffer, with 45 mM KCl and [$Mn^{2+}$] between 50 and 150 nM. The pH of the samples was maintained at 7.8 in these experiments. Studies utilizing $HPO_3^{2-}$ are impractical at lower pH where the probe undergoes dynamic proton exchange ($pK_A$=6.0) leading to significant shortening of the diamagnetic $^{31}P$ $T_2$.

Fluorescence polarization studies of RSG1.2/RNA binding: Samples containing the N-terminally TAMRA labeled peptide, RSG1.2 (3 nM) and either RRE1 or RRE2 (concentrations ranging from 0.1 to 200 nM) were prepared in Reaction Buffer (10 mM Hepes-KOH pH 7.5; 150 mM KCl; 5 mM $MgCl_2$; 1 mM DTT; 1% glycerol; 50 µg/ml BSA; 100 µg/ml Hen-Egg Lysozyme). Each sample was irradiated at 530 nM and the polarization of the fluorescent emission at 580 nM was recorded using a LJL Analyst (Molecular Devices Corp. Sunnyvale, Calif.). Measurements repeated at 1, 15, and 30 min showed no evidence of change with time.

Figure 14:
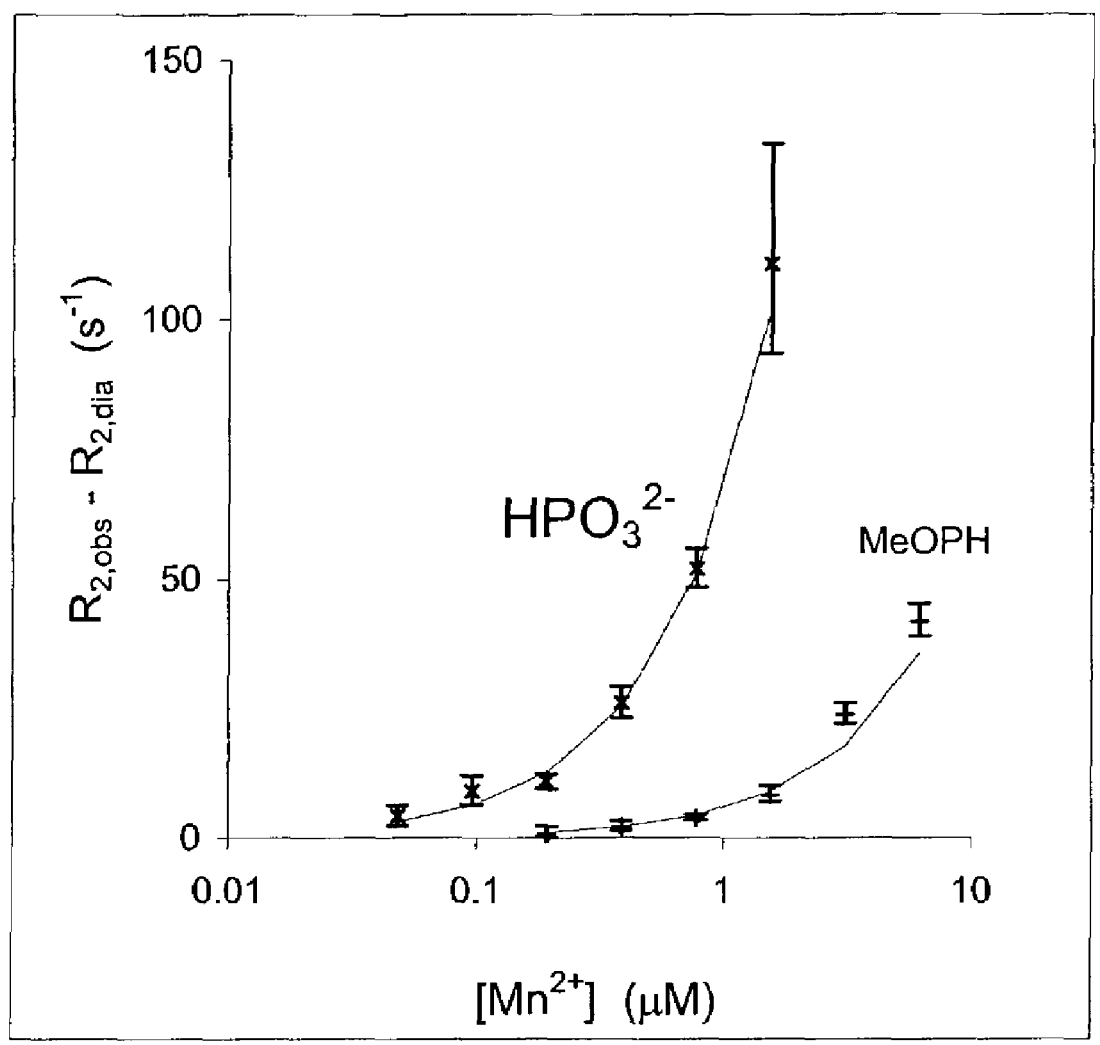
FIG. 14 is a semi-log plot showing the effects of [$Mn^{2+}$] on $^{31}$P transverse relaxation rates ($R_{2,obs}$) of phosphite dianion ($HPO_3^{2-}$, represented by the X within the error bars) and methyl phosphite anion ($CH_3OP(H)O_2^-$, represented by a +), corrected for diamagnetic relaxation rate ($R_{2,dia}$). $R_2$ of $HPO_3^{2-}$ is a factor of ten more sensitive to [$Mn^{2+}$] than the $R_2$ of MeOPH. Lines show behavior predicted for relaxation enhancement proportional to [$Mn^{2+}$].
Figure 15:
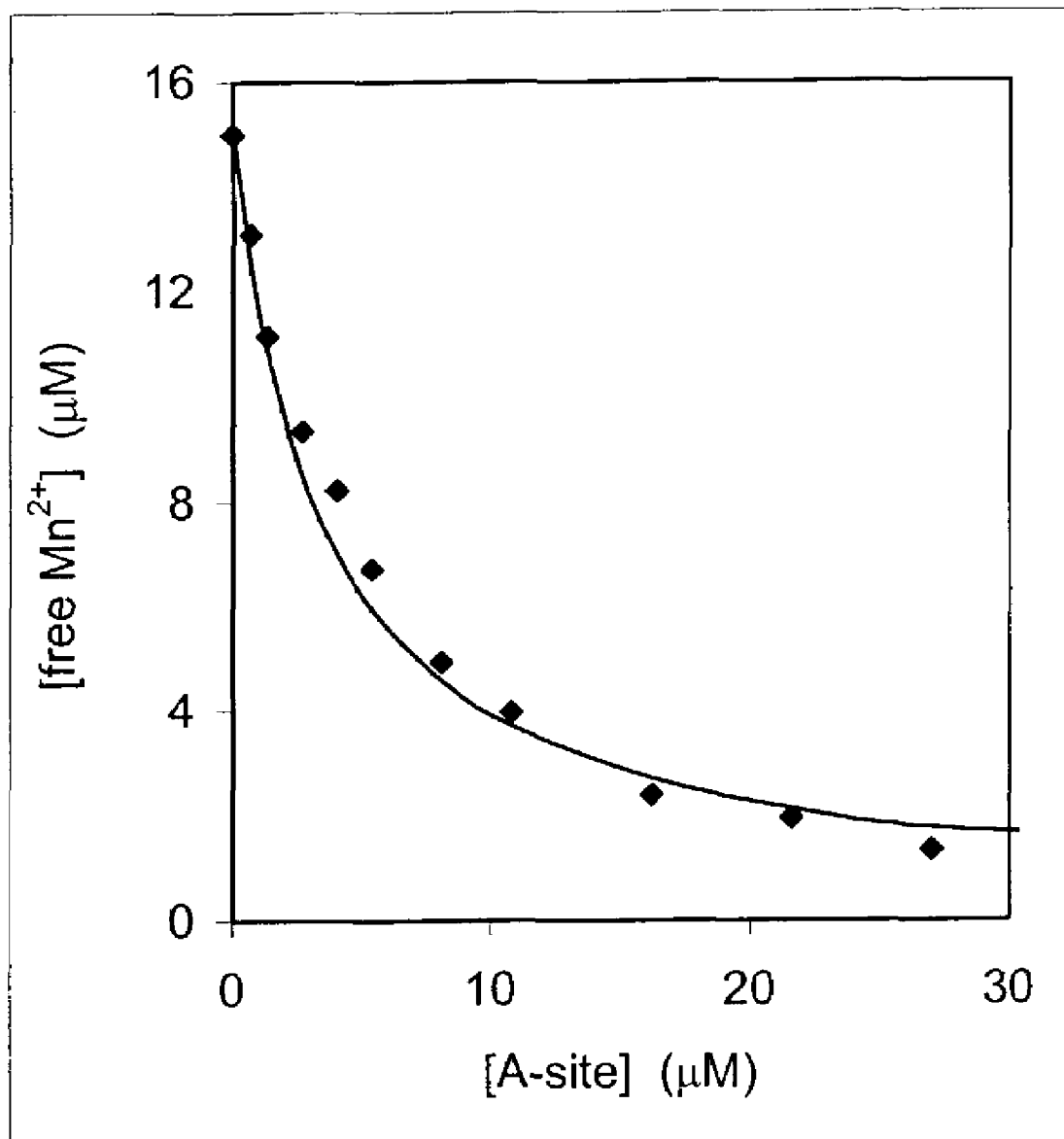
FIG. 15 is a graph of the effect of A-site RNA on free $Mn^{2+}$ (5 mM PIPES, pH 7.2, 5 mM MeOPH, K$^+$ salts). The line represents behavior predicted for 7 independent binding sites having $K_{d,Mn}$=25 µM.

Measurable $Mn^{2+}$ binding occurs under a useful range of [RNA]. The sensitivities of the $^{31}P$ $T_2$ NMR relaxation rates of phospite ($HPO_3^{2-}$) and methyl phosphite (MeOPH) to $Mn^{2+}$ make it possible to measure [$Mn^{2+}$] accurately at sub-micromolar levels (FIG. 14) (Summers et al. Inorg. Chem., 2001, 40: 6547–6554). Titration of each of the four RNAs into solutions containing $Mn^{2+}$ (3 µM), MeOPH (5 mM), and PIPES buffer (5 mM, pH 7.2) caused a diminution of the MeOPH $^{31}P$ transverse relaxation rate (R2), indicating that the RNAs sequestered the $Mn^{2+}$. The effect of the A-site construct on free [$Mn^{2+}$] (FIG. 15) is typical. In 12 mM K⁺, the three hairpins bound half the available $Mn^{2+}$ at much lower concentrations (3 to 7 µM) than was required for U31 (~50 µM). At 100 µM, the affinity of each hairpin RNA was sufficient that relaxation enhancement of the probe by 3 µM $Mn^{2+}$ was undetectable. Since efficient relaxation enhancement requires inner sphere contact between MeOPH and the $Mn^{2+}$ ion (Summers et al. Inorg. Chem., 2001, 40: 6547–6554), this result indicates that the anionic probe does not contact the RNA complexed metal ion. Thus, the $^{31}P$ $T_2$ relaxation enhancement of MeOPH can be used to measure the concentration of free $Mn^{2+}$ ion without interference by RNA complexed $Mn^{2+}$.

While these experiments provide an accurate measure of the concentration of free $Mn^{2+}$, the certainty of $Mn^{2+}$ dissociation constants ($K_{d,Mn}$) derived from such data is limited by the uncertainty in the number of discreet binding sites. The line in FIG. 15 was produced assuming that the RNA has 7 non-interacting binding sites, each with $K_{d,Mn}$=25 µM. We note, however, that the data fit just as well to a model with 8 or more binding sites having higher $K_{d,Mn}$ values. A Scatchard analysis of binding data would require knowledge of RNA saturation which is not available from this technique. Additional uncertainty is introduced by the potential presence of trace impurities (diamagnetic metal ions, and/or high affinity chelating agents such as EDTA) in the RNA samples. We feel that our K⁺, $Mg^{2+}$, neomcyin b, and RSG1.2 samples are not nearly as prone to contamination as the RNA samples and have greater confidence in values derived from experiments wherein the concentration of the cation is varied. The 25 µM value is well within the range of dissociation constants published for $Mn^{2+}$/RNA interactions: in 0.1 M NaCl, the hammerhead ribozyme reportedly binds four $Mn^{2+}$ ions with $K_{d,Mn}$~4 µM and another five with $K_{d,Mn}$~460 µM (Hoogstraten et al. J. Am. Chem. Soc., 2002, 124: 834–842).

Figure 16:
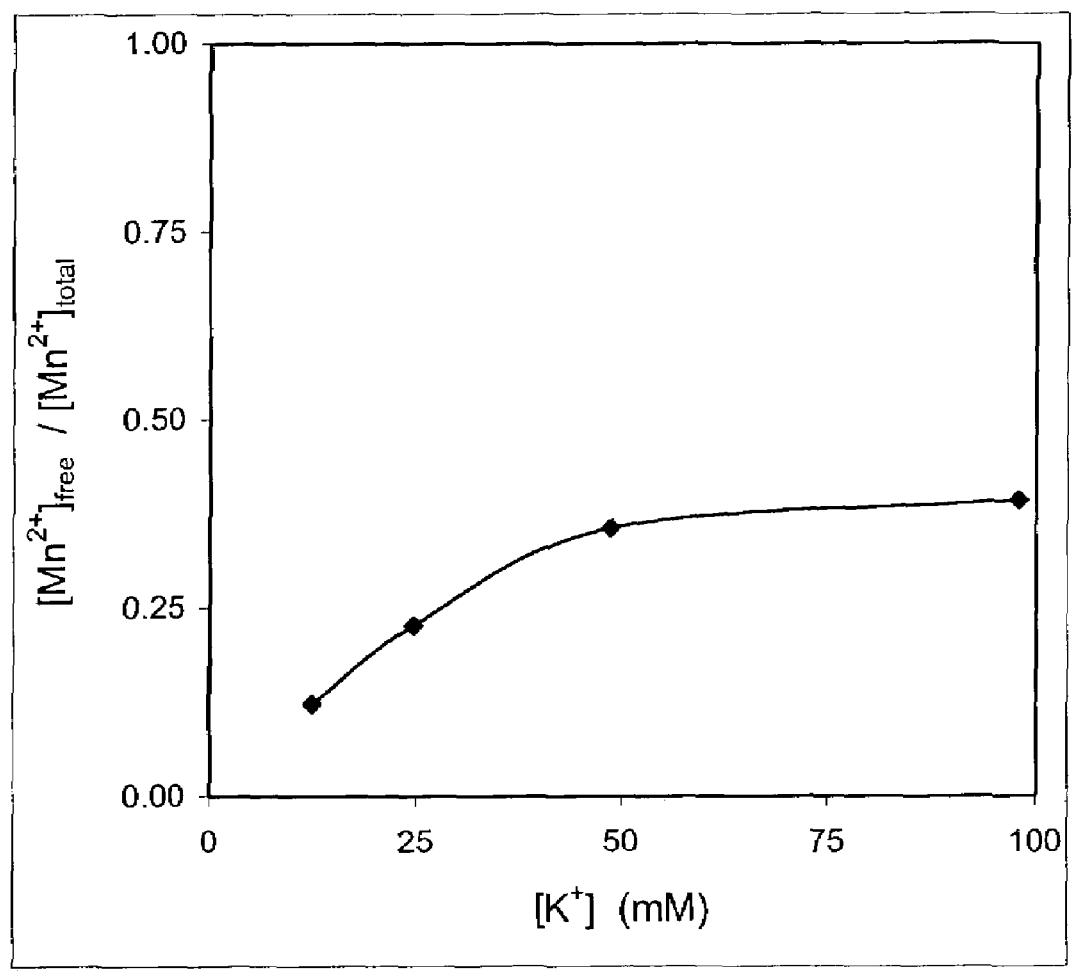
FIG. 16 is a graph of the effect of [K$^+$] on free $Mn^{2+}$ in solutions of A-site (27 µM) and $Mn^{2+}$ (16 µM), as determined from $R_2$ data (FIG. 14).

As observed in earlier studies, $Mn^{2+}$/RNA binding was strongly influenced by the concentration of monovalent ions. At [K⁺]<20 mM, addition of KCl solution results in increased relaxation enhancement, above 40 mM, however, the K⁺ association becomes saturated and further addition of KCl had little effect. The effect of [K⁺] on $Mn^{2+}$ binding by the A-site construct is presented in FIG. 16. The effects of K⁺ on $Mn^{2+}$ binding by the RNAs were sequence dependent. While 30 mM K⁺ displaced all the $Mn^{2+}$ from $U_{31}$, 150 mM K⁺ did not displace all the $Mn^{2+}$ from any of the three hairpins. This result indicates that the hairpins contain discrete binding sites that are selective for divalent metals and that $U_{31}$ does not. We considered the possibility that high [K⁺] might allow contact between the probe ion and the RNA bound $Mn^{2+}$. This hypothesis was inconsistent with the results of experiments comparing the relaxation enhancements of the two probes; MeOPH and $HPO_3^{2-}$. The two probes (which have different electronic charges) should differ in sensitivity to the electronic environment of the $Mn^{2+}$. This reasoning was borne out by experiments comparing the relative sensitivities of MeOPH and $HPO_3^{2-}$ toward relaxation by $Mn^{2+}$ in the presence and absence of EDTA. Relaxation of the di-anionic probe $HPO_3^{2-}$ by the anionic metal complex ($MnEDTA^{2-}$) was found to be significantly slower than that of the mono-anionic probe (MeOPH) (Results not shown). While addition of K⁺ to $Mn^{2+}$ containing solutions of RRE1, caused an increase in the relaxation rates of both probes, the ratio of the two remained equal to that observed in the absence of the RNA. Since the electronic charge environment surrounding the complexed $Mn^{2+}$ should be significantly different than that of the free ion, this result indicates that addition of K⁺ causes an increase in the concentration of free $Mn^{2+}$, which is the sole species responsible for probe nucleus relaxation in these experiments. The decrease in $Mn^{2+}$ affinity is likely to stem from a combination of two effects: First, K⁺ is able to compete with $Mn^{2+}$ for non-specific electrostatic interactions, and second, neutralization of the anionic charge causes a decrease in the affinity of specific divalent metal sites.

$Mn^{2+}$ is displaced from RNA by $Mg^{2+}$ in competition experiments. To determine whether $Mn^{2+}$ was bound at sites on the RNA molecules that bind $Mg^{2+}$ in vivo, we titrated solutions containing $Mn^{2+}$ and the RNAs with $MgCl_2$ solution and monitored the effect using the PhoRE technique. The effect of $Mg^{2+}$ on $Mn^{2+}$ binding by $U_{31}$ was that expected for competition between two identical cations for association with an indiscriminate poly-anion; the probe $R_2$ increased with [$Mg^{2+}$] until the concentrations of the two ions were similar. After the [$Mg^{2+}$] had exceeded about twice the [$Mn^{2+}$], addition of more $Mg^{2+}$ had no measurable effect.

Figure 17:
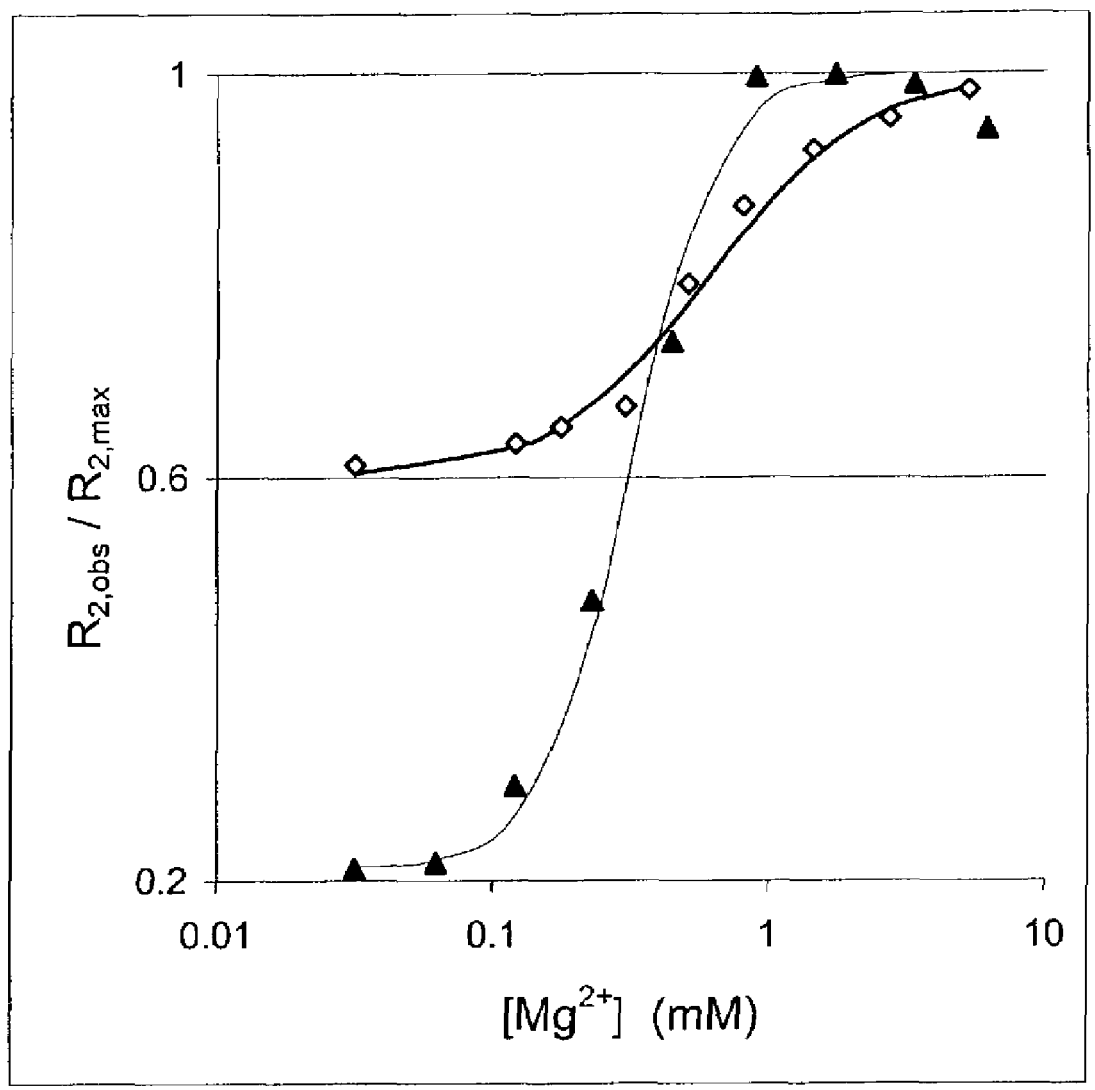
FIG. 17 is a graph of the effect of [$Mg^{2+}$] on MeOPH relaxation in solutions of RRE1 (20 µM) in 25 mM K$^+$ (filled triangles) or 100 mM K$^+$ (open diamonds) and $Mn^{2+}$ (3 µM). Solid lines show behavior predicted by the $K_d$ and n values in Table 1.

$Mn^{2+}$ bound by the hairpins was displaced by $Mg^{2+}$ in a manner more consistent with the metals being bound in a well defined complex. The effects of [$Mg^{2+}$] on $Mn^{2+}$ binding by RRE1 at two different [K⁺] are presented in FIG. 17. Titration curves were interpreted in terms of a model that assumes that [$Mn^{2+}$]<<$K_{d,Mn}$ and that the $Mg^{2+}$ binding equilibrium is governed by the Hill equation. Under these conditions the effect of [$Mg^{2+}$] on the observed relaxation rate ($R_{2,obs}$) is governed by Eq (1):

$$(Q-Q_0)/Q_0 = (1/K_{d,Mg})[Mg]^n \qquad (1)$$

where $Q=(R_{2,obs}-R_{2,dia})/(R_{2,max}-R_{2,obs})$, $R_{2,dia}$ and $R_{2,max}$ represent the values of $R_2$ in diamagnetic solutions and the maximum value observed, respectively. The term $Q_0$ (defined as $Q_0=K_{d,Mn}/RNA$) arises from the competitive nature of the experiment, and represents the value of Q observed in the absence of added $Mg^{2+}$. The presence of $Q_0$ in Eq (1) introduces a minor complication in the interpretation of the data which can be illustrated by considering the data presented in FIG. 17. While the concentrations of $Mg^{2+}$ required to release half the bound $Mn^{2+}$ were similar for the two experiments (300 and 600 µM), $Q_0$ values were significantly different. As a result $K_{d,Mg}$ determined in 25 mM $K^+$ was considerably lower than in 100 mM $K^+$ (64 versus 360 µM, Table 1).

TABLE 1

Equilibrium coefficients for $Mg^{2+}$ binding by RNA constructs.

| RNA | $K_{d,Mg}$ (µM) (Hill Coefficient) | |
|---|---|---|
| | 25 mM $K^+$ | 100 mM $K^+$ |
| $U_{31}$ | none | |
| A-site | 55 (0.8) | 154 (1.0) |
| RRE1 | 64 (2.8) | 360 (1.5) |
| RRE2 | | 344 (1.0) |

Using the analysis described above, values of $K_{d,Mg}$ and n were determined for A-site and RRE1 at low [$K^+$] and at saturating [$K^+$] (Table 1). Like RRE1, the A-site also showed a marked decrease in $Mg^{2+}$ affinity at the higher [$K^+$]. The decrease in $Mg^{2+}$ affinity at the higher [$K^+$] mirrors the decrease in $Mn^{2+}$ affinity noted above. All the values in Table 1 are well within the range of those found in the literature; values of $K_{d,Mg}$ ranging from 1 µM to 2 mM have been reported for transfer RNAs alone (Schimmel et al. *Ann Rev. Biophys. Bioeng.*, 1980, 9: 181–221).

Figure 18:
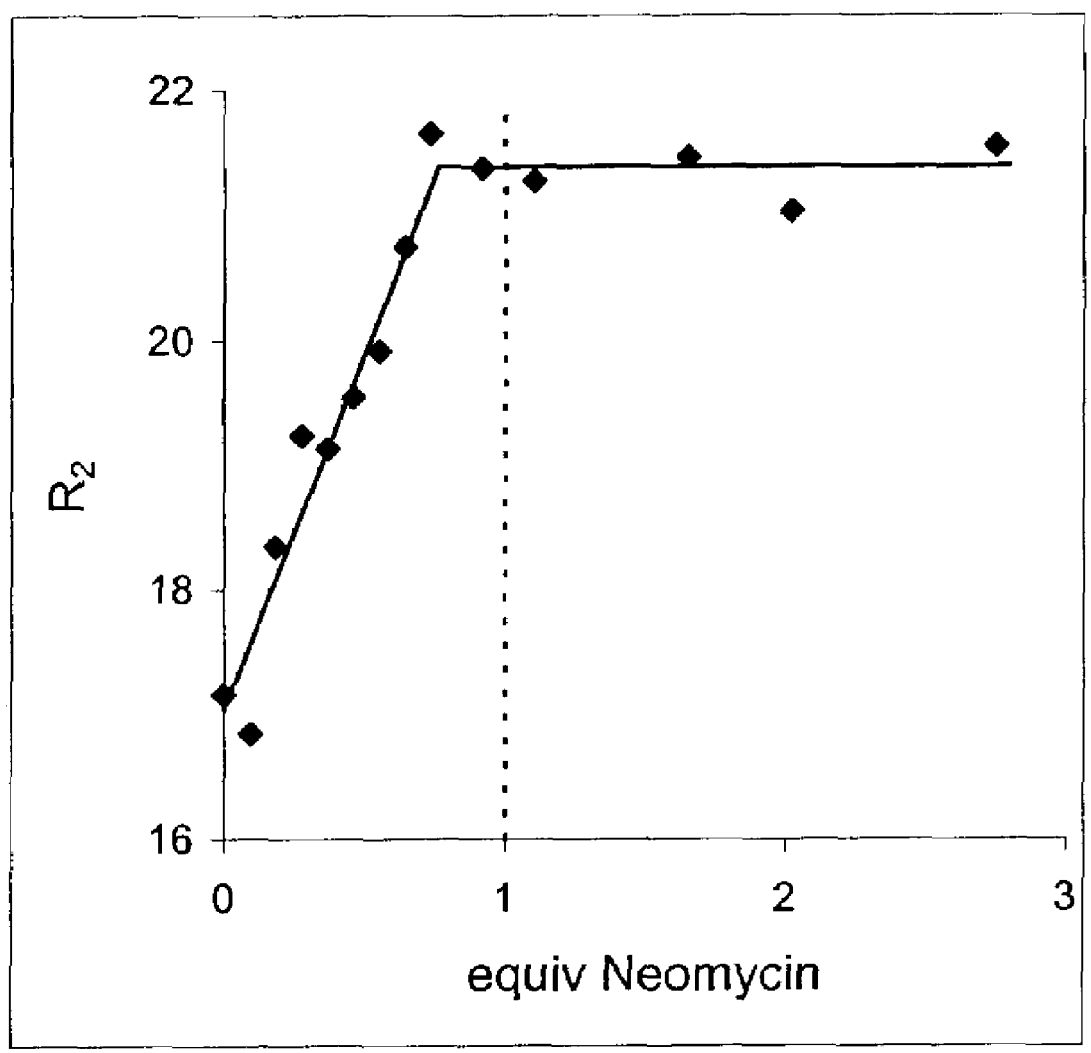
FIG. 18 is a graph of the effect of neomycin b on the relaxation rate ($R_2$) of the $HPO_3^{2-}$ $^{31}$P signal in solutions of A-site RNA (2.7 uM), $Mn^{2+}$ (0.11 uM), and 100 mM K$^+$.

Neomycin b reacted with each of the hairpins, causing a release of $Mn^{2+}$. The $Mn^{2+}$ release was proportional to the added neomycin until the RNA was saturated. After saturation, continued addition of neomycin had no effect on MeOPH relaxation (FIG. 18). The ratio of neomycin to RNA at the saturation point was dependant on the RNA sequence, [$K^+$], and [RNA]. At [RNA]=2.7 µM (100 mM $K^+$), the A-site construct bound a single equivalent of neomycin (FIG. 18). At [RNA]=27 µM, however, the same construct bound 3 equivalents (data not shown). Both RRE1 and RRE2 constructs bound multiple equivalents of neomycin under each condition studied. Thus, of the three hairpins, only the A-site construct bound neomycin in a 1:1 complex, and only at RNA<3 µM. The low selectivity for neomycin binding should not be surprising since the antibiotic is known to bind a wide variety of RNAs with varying affinities (Hendrix et al. *J. Am. Chem. Soc.*, 1997, 119: 3641–3648; Sannes-Lowery et al. *Anal. Biochem.*, 2000, 280: 264–271. ). We note that another RRE1 model bound three equivalents of neomycin b (Harada et al. Nature, 1996, 380: 175–179).

Figure 19:
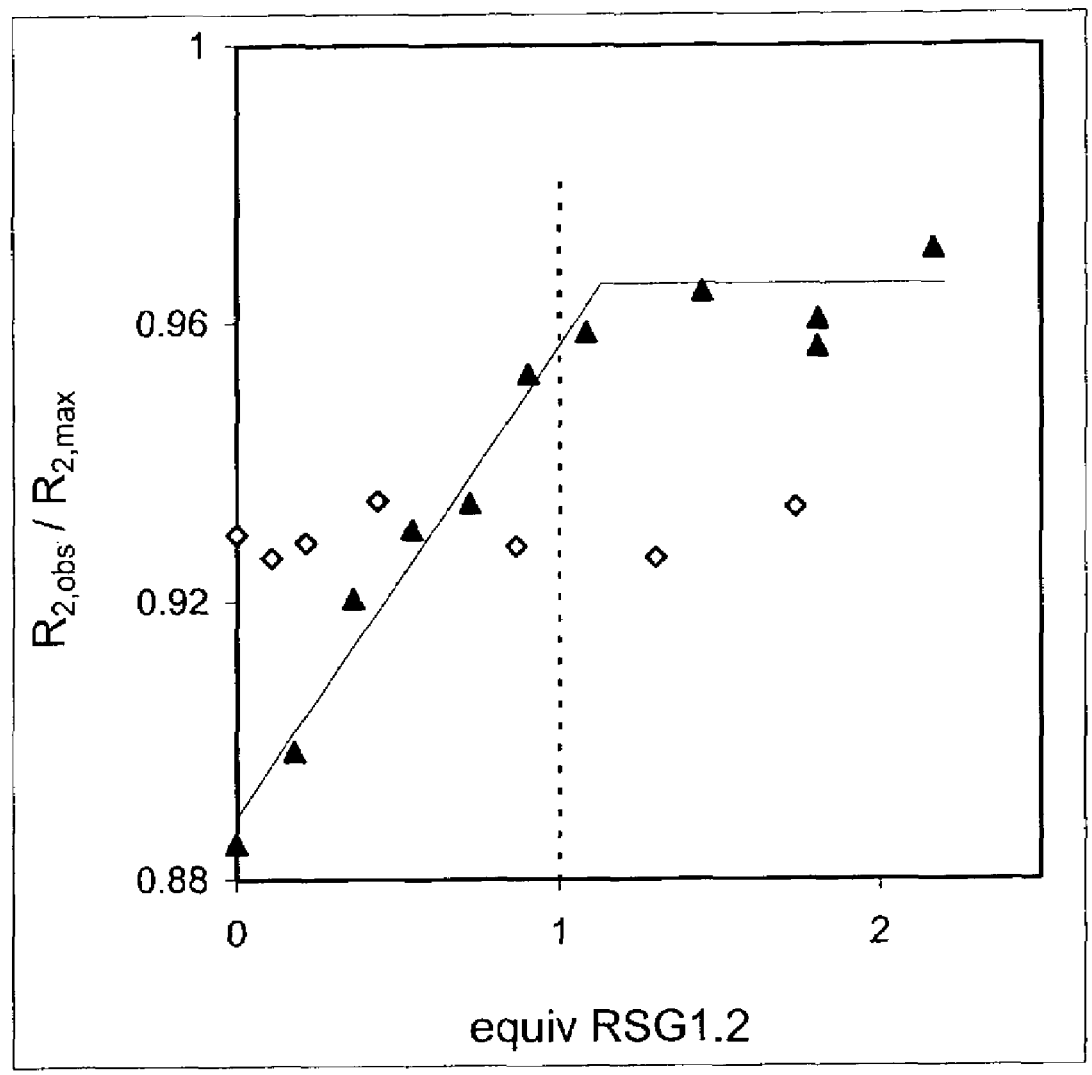
FIG. 19 is a graph of the effect of RSG1.2 on $Mn^{2+}$ binding by either 2.7 µM RRE1 (filled triangles) or 3.0 µM RRE2 (open diamonds) in 100 mM K$^+$. Values were normalized to the $R_2$ value, obtained upon addition of 2 mM $Mg^{2+}$.
Figure 20:
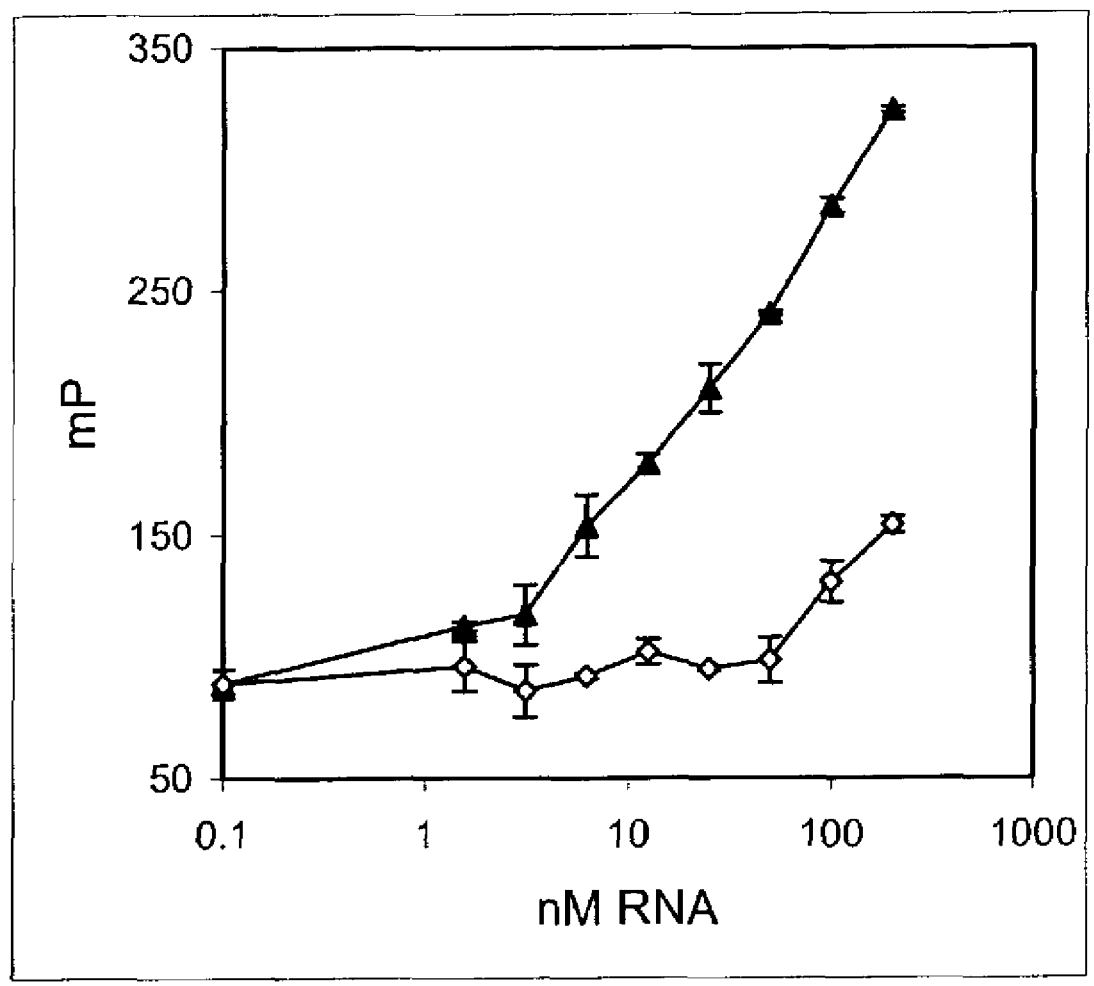
FIG. 20 is a graph of the effect of [RRE1] (filled triangles) and [RRE2] (open diamonds) on fluorescence polarization of TAMRA labeled RSG1.2.

Binding RSG1.2 Peptide to RNA constructs was also strongly dependent on RNA sequence, [RNA] and [$K^+$]. At <3 µM RNA, 100 mM $K^+$, the RRE1 construct bound a single equivalent of RSG1.2 (FIG. 19). Under these conditions neither the RRE2 construct, nor the A-site bound the peptide. At higher RNA (>20 µM), each RRE construct bound multiple equivalents of RSG1.2, releasing $Mn^{2+}$, resulting in precipitation of the RNA/peptide complex. The results of our PhoRE studies of RSG1.2 /RNA binding are consistent with those of our fluorescence polarization studies of this system. The effects of RRE1 and RRE2 on fluorescence polarization of TAMRA labeled RSG1.2 are presented in FIG. 20. Low levels of RRE1 cause an increase in polarization consistent with complexation of the peptide and an increase in effective mass. A similar level of polarization requires a fifty fold greater concentration of RRE2, indicating a weaker interaction between the peptide and this RNA.

Our results demonstrate that PhoRE represents a viable method for studying the interactions of metal ions, small molecules, and peptides with nucleic acids. We describe evidence for discreet divalent metal binding sites on three hairpin RNAs. We found that $Mg^{2+}$ is able to compete with $Mn^{2+}$ at physiological concentrations, indicating that small molecules, peptides, or proteins that displaces $Mn^{2+}$ from an RNA should bind in vivo by displacing $Mg^{2+}$.

Other Embodiments

Modifications and variations of the described methods of the invention will be apparent to those skilled in the art without departing from the scope and spirit of the invention. Although the invention has been described in connection with specific desirable embodiments, it should be understood that the invention as claimed should not be unduly limited to such specific embodiments. Indeed, various modifications of the described modes for carrying out the invention, which are obvious to those skilled in the field of chemistry or related fields, are intended to be within the scope of the invention.

All publications, patents, and patent applications mentioned in this specification are herein incorporated by reference to the same extent as if each individual publication, patent, or patent application was specifically and individually to be incorporated by reference.

Other embodiments are in the claims.

What is claimed is:

1. A method of detecting the binding of a species to a nucleic acid, said method comprising the steps of:
   (a) measuring a magnetic relaxation property of a probe in a first solution using nuclear magnetic resonance spectroscopy, wherein said first solution comprises said nucleic acid, a first concentration of said species, a paramagnetic metal ion, and said probe;
   (b) measuring the magnetic relaxation property of said probe in a second solution using nuclear magnetic resonance spectroscopy, wherein said second solution comprises said nucleic acid, a second concentration of said species, a paramagnetic metal ion, and said probe; and
   (c) comparing the relaxation property measured in step (a) with the relaxation property measured in step (b), wherein a difference in said relaxation properties indicates the binding of said species to said nucleic acid.

2. The method of claim 1, wherein, in step (c), said magnetic relaxation properties of said probe are correlated with said first and second concentrations of said species, thereby quantifying the binding of said species to said nucleic acid.

3. The method of claim 1, wherein said first concentration is 0.0 µM.

4. The method of claim 1, wherein said species is a divalent metal ion.

5. The method of claim 4, wherein said metal ion is $Mg^{2+}$.

6. The method of claim 1, wherein said species is a candidate therapeutic agent.

7. The method of claim 6, wherein said candidate therapeutic agent is selected from a molecular library.

8. The method of claim 1, wherein said species is selected from the group consisting of a protein, a peptide, and a fragment of a protein.

9. The method of claim 1, wherein said paramagnetic metal ion is selected from the group consisting of $Mn^{2+}$, $Fe^{2+}$, $Fe^{3+}$, $Co^{2+}$, $Ni^{2+}$, or a lanthanide ion.

10. The method of claim 1, wherein said paramagnetic metal ion is bound to said nucleic acid.

11. The method of claim 1, wherein said probe comprises an X—H bond, wherein X is an NMR-active nucleus.

12. The method of claim 11, wherein X is $^{31}P$.

13. The method of claim 12, wherein said probe is methylphosphite, ethylphosphite, or ethylphosphonite.

14. The method of claim 11, wherein said magnetic relaxation property of X is indirectly detected using X edited, $^1H$ detected NMR spectroscopy.

15. The method of claim 14, wherein said measuring of said magnetic relaxation properties of X proceeds by the steps of:
    (i) using a pulse sequence to transfer coherent magnetization originating on the $^1H$ nucleus to the X nucleus by Insensitive Nuclei Enhanced by Polarization Transfer (INEPT) techniques prior to a $T_2$ delay;
    (ii) providing a $T_2$ delay; and
    (iii) transferring the remaining coherence back to the $^1H$ nucleus for detection using a reverse INEPT series of pulses.

16. The method of claim 1, wherein said magnetic relaxation property is the $T_2$ relaxation of a nucleus of said probe.

17. The method of claim 1, wherein said nucleic acid comprises RNA.

18. The method of claim 1, wherein said nucleic acid comprises DNA.

19. The method of claim 1, wherein said nucleic acid is double-stranded.

20. A method of detecting the binding of a paramagnetic metal ion to a nucleic acid, said method comprising the steps of:
    (a) measuring a magnetic relaxation property of a probe in a first solution using nuclear magnetic resonance spectroscopy, wherein said first solution comprises a first concentration of said paramagnetic metal ion, said nucleic acid, and said probe;
    (b) measuring the magnetic relaxation property of said probe in a second solution using nuclear magnetic resonance spectroscopy, wherein said second solution comprises a second concentration of said paramagnetic metal ion, said nucleic acid, and said probe; and
    (c) comparing the relaxation property measured in step (a) with the relaxation property measured in step (b), wherein a difference in said relaxation properties indicates the binding of said paramagnetic metal ion to said nucleic acid.

21. The method of claim 20, wherein, in step (c), said magnetic relaxation properties of said probe are correlated with said first and second concentrations of said nucleic acid, thereby quantifying the binding of said paramagnetic metal ion to said nucleic acid.

22. The method of claim 20, wherein said first concentration is 0.0 µM.

23. The method of claim 20, wherein said paramagnetic metal ion is selected from the group consisting of $Mn^{2+}$, $Fe^{2+}$, $Fe^{3+}$, $Co^{2+}$, $Ni^{2+}$, or a lanthanide ion.

24. The method of claim 1, wherein said probe comprises an X—H bond, wherein X is an NMR-active nucleus.

25. The method of claim 18, wherein X is $^{31}P$.

26. The method of claim 25, wherein said probe is methylphosphite, ethylphosphite, or ethylphosphonite.

27. A method of determining the effect of a first species on the binding of a second species to a nucleic acid, said method comprising the steps of:
    (a) measuring a magnetic relaxation property of a probe in a first solution using nuclear magnetic resonance spectroscopy, wherein said first solution comprises a first concentration of said first species, said nucleic acid, said second species that binds to said nucleic acid, a paramagnetic metal ion, and a probe;
    (b) measuring the magnetic relaxation property of said probe in a second solution using nuclear magnetic resonance spectroscopy, wherein said second solution comprises a second concentration of said first species, said nucleic acid, said second species, said paramagnetic metal ion, and said probe; and
    (c) comparing the relaxation property measured in step (a) with the relaxation property measured in step (b), wherein a difference in said relaxation properties indicates the inhibition of the binding of said second species to said nucleic acid.

28. The method of claim 27, wherein, in step (c), said magnetic relaxation properties of said probe are correlated with said first and second concentrations of said first species, thereby quantifying the effect of said first species on the binding of said second species to said nucleic acid.

29. The method of claim 27, wherein said first concentration is 0.0 µM.

30. The method of claim 27, wherein one of said first species and said second species is a divalent metal ion.

31. The method of claim 30, wherein said metal ion is $Mg^{2+}$.

32. The method of claim 27, wherein said first species or said second species is a candidate therapeutic agent.

33. The method of claim 32, wherein candidate therapeutic agent is selected from a molecular library.

34. The method of claim 27, wherein said first or said second species is selected from the group consisting of a protein, a peptide, and a fragment of a protein.

35. The method of claim 27, wherein said paramagnetic metal ion is selected from the group consisting of $Mn^{2+}$, $Fe^{2+}$, $Fe^{3+}$, $Co^{2+}$, $Ni^{2+}$, or a lanthanide ion.

36. The method of claim 27, wherein said paramagnetic metal ion is bound to said nucleic acid.

37. The method of claim 27, wherein said probe comprises an X—H bond, wherein X is an NMR-active nucleus.

38. The method of claim 27, wherein X is $^{31}P$.

39. The method of claim 38, wherein said probe is methylphosphite, ethylphosphite, or ethylphosphonite.

40. A method of detecting the availability of a paramagnetic metal ion in a solution comprising a nucleic acid, said method comprising the steps of:
    (a) providing a solution comprising said nucleic acid, a probe, and said paramagnetic metal ion and
    (b) measuring a magnetic relaxation property of said probe in said solution using nuclear magnetic resonance spectroscopy, wherein the magnitude of said magnetic property is indicative of the availability of said paramagnetic ion in said solution.

41. The method of claim 40, wherein said paramagnetic metal ion is bound to said nucleic acid.

* * * * *